(12) United States Patent
Glozman

(10) Patent No.: US 7,271,146 B2
(45) Date of Patent: Sep. 18, 2007

(54) METHODS FOR TREATMENT OF HELICOBACTER PYLORI-ASSOCIATED DISORDERS

(75) Inventor: Sabina Glozman, Rehovot (IL)

(73) Assignee: Vecta Ltd., Rehovot (IL)

( * ) Notice: Subject to any disclaimer, the term of this patent is extended or adjusted under 35 U.S.C. 154(b) by 0 days.

(21) Appl. No.: 10/682,937

(22) Filed: Oct. 14, 2003

(65) Prior Publication Data

US 2004/0082514 A1  Apr. 29, 2004

(30) Foreign Application Priority Data

Oct. 14, 2002  (IL)  ..................... 152289

(51) Int. Cl.
*A61K 38/00* (2006.01)
*A61K 49/00* (2006.01)

(52) U.S. Cl. .............. 514/2; 514/12; 514/17; 514/18; 530/300; 424/9.1; 435/243; 435/7.1

(58) Field of Classification Search ............ 514/2, 514/12, 17, 18; 435/7.1, 243; 424/9.1; 530/300
See application file for complete search history.

(56) References Cited

U.S. PATENT DOCUMENTS

| | | | |
|---|---|---|---|
| 4,891,356 A | 1/1990 | Szabo | 514/2 |
| 5,840,737 A | 11/1998 | Phillips | 514/338 |
| 6,489,346 B1 | 12/2002 | Phillips | 514/338 |
| 6,645,988 B2 | 11/2003 | Phillips | 514/338 |
| 6,699,885 B2 | 3/2004 | Phillips | 514/338 |
| 6,780,882 B2 | 8/2004 | Phillips | 514/338 |
| 2001/0020005 A1 | 9/2001 | Chowers et al. | 514/18 |
| 2003/0096012 A1* | 5/2003 | Besse et al. | 424/489 |

FOREIGN PATENT DOCUMENTS

| | | |
|---|---|---|
| EP | 1 087 783 B1 | 4/2004 |
| WO | WO99/65513 | 12/1999 |
| WO | WO 01/022985 * | 4/2001 |
| WO | WO 01/22985 | 4/2001 |

OTHER PUBLICATIONS

Nagata et al., Antimicrobial Agents and Chemotherapy 39 (2), 567-570 (1995)).*
Gaw et al., "Role of pepsin in the development of indomethacin-induced antral ulceration in the rat", *Ailment Pharmacol Ther*, vol. 9, pp. 167-172 (1995).
Bonnevie et al., "Double-blind randomized clinical trial of a pepsin-inhibitory pentapeptide (pepstatin) in the treatment of duodenal ulcer", *Gut*, vol. 20, pp. 624-628 (1979).
Piper et al., "pH stability and activity curves of pepsin with special reference to their clinical importance", *Gut*, vol. 6, pp. 506-508 (1965).
Ayalon, A. et al., "Does Luminal Gastrin Stimulate Gastric Acid Secretion?" *Am. J. Surg.*, vol. 141, pp. 94-97 (1981).
De Graef, et al., "Influence of the Stimulation State of the Parietal Cells on the Inhibitory Effect of Omeprazole on Gastric Acid Secretion in Dogs," *Gastroenterology*, vol. 91, pp. 333-337 (1985).
Fiddian-Green, R.G. et al., "A physiological role for luminal gastrin?" *Surgery*, vol. 83, No. 6, pp. 663-668 (1978).
Martindale Thirty-second edition, p. 1616, "Supplementary Drugs and Other Substances, 1999."
Morrell, M.T. et al., "Absorption of Pentagastrin from Gastrointestinal Tract in Man," *Lancet*, vol. 2, No. 7937, p. 712 (1975).

* cited by examiner

Primary Examiner—Chih-Min Kam
(74) Attorney, Agent, or Firm—Fennemore Craig PC

(57) ABSTRACT

The present invention relates to methods for treating pathological conditions associated with *Helicobacter* sp infections, specifically *H. pylori* infection. The present invention further relates to methods for treating pathologies characterized by excess gastric acid secretion. The methods of the present invention comprise oral administration of pentagastrin effective locally in the stomach in conjunction with a gastric proton pump inhibitor. It is disclosed herein for the first time that PG administered orally exerts a local effect in the stomach and may be used in combination with a PPI for treating pathological conditions characterized by excess gastric acid secretion and in pathological conditions associated with *Helicobacter* sp infections.

19 Claims, 13 Drawing Sheets

METHODS FOR TREATMENT OF *HELICOBACTER PYLORI*-ASSOCIATED DISORDERS

CROSS-REFERENCE TO RELATED APPLICATIONS

This application claims priority to Israeli Patent Application No. 152289, filed Oct. 14, 2002.

FIELD OF THE INVENTION

The present invention relates to methods for the treatment and/or prevention of *Helicobacter pylori*-associated disorders particularly intended for local, intra-gastric eradication of *H. pylori*.

BACKGROUND OF THE INVENTION

Peptic ulcers, once thought to result from stress, excess acidity, or a reduction of the mucosal defense factors in the stomach, are now in a majority of cases considered to be the result of bacterial infection by *Helicobacter pylori* (*H. pylori*). The involvement of *H. pylori* in peptic ulcers is well documented in "*Helicobacter pylori* in Peptic Ulceration and Gastritis", edited by Barry J. Marshall, Richard W. McCallum and Richard L. Guerraut, Blackwell Scientific Publications, Boston, U.S.A. The effect of treatment of *H. pylori* infections on long-term recurrence of gastric or duodenal ulcer is described by David Y. Graham et al. In Annals of Internal Medicine 1992; 116: No. 9.

*H. pylori* resides within the mucous layer of the human gastric mucosa. Due to extremely low pH, the stomach is a hostile environment to most other microorganisms. The ability of *H. pylori* to flourish in the stomach has been attributed to protective mechanisms such as the production of urease, protecting the bacterium from gastric acidity by creating a basic microenvironment [Taylor D. N. and Blaser M. J., Epidemiol Rev (1991) 13:42-59].

Presently, the main therapies employed in the treatment of chronic active gastritis and peptic ulcer diseases include agents for reducing the stomach acidity for example the histamine H2-receptor antagonists which result in the suppression of acid and pepsin secretion, and proton pump inhibitors which act by inhibition of the parietal cell $H^+/K^+$ ATPase, responsible for acid secretion from these cells. Proton pump inhibitors (PPIs) e.g. omeprazole and its pharmaceutically acceptable salts are disclosed for example in EP 124495. U.S. Pat. No. 5,093,342 disclosed that omeprazole may be used also as an effective anti-bacterial agent.

Other therapies for *H. pylori* infections include bismuth compounds and antibiotics. However, currently used treatment modalities are problematic, since post-treatment relapse rates are rising. In addition, several of these therapies are accompanied by significant side effects. For example, effective antibiotic treatment of *H. pylori* infections requires treatment over an extended duration (1-2 weeks) and may result in the induction of diarrhea and intestinal discomfort. The bismuth compounds are also known to have a number of significant undesirable side effects.

Current antibiotic treatment for *H. pylori* infections usually consists of combinations of two antibiotic agents together with an adjunctive agent, which is usually either a PPI or H2 blockers. Antibiotic resistance of *H. pylori* is increasing in prevalence [Hazell, SL, Eur J Clin Infect Dis (1999) 18:83-86]. Triple therapy regimen (Tetracycline, in combination with metronidazole and tripotassium dicitrato-bismuthate (TDB) has been found to be more effective than mono-therapy, but patient compliance and drug resistance further limits its applicability.

U.S. Pat. No. 5,196,205 (corresponding to patent application WO 89/03219) describes a method for the treatment of *H. pylori* infections, consisting of the administration of a bismuth compound, an antibiotic belonging to the groups of penicillins and tetracycline, and a second antibiotic, such as metronidazole. The relevant therapy thus consists of the administration of three medications (one for each active principle) several times a day.

There are also other patents and patent applications describing single or multiple therapies for the eradication of *H. pylori*, such as U.S. Pat. Nos. 5,472,695, 5,560,912, 5,582,837, WO 92/11848 and WO 96/02237. None of these patents and patent applications overcome the problem of the interaction between active principles in a simple and efficient manner.

It has been previously shown by one of the present inventors that the human hormone gastrin serves as a growth factor for the bacterium (Chowers et al., 1999, Gastroenterology 1999 117(5):1113-8). This observation led to the finding that gastrin analogues, particularly the gastrin molecule C-terminal such as pentagastrin (PG), inhibit the growth enhancing effect of gastrin on *H. pylori*, and can thus be used in the eradication of this bacterium (WO 99/65513).

According to the present art, PG is typically used as a diagnostic agent for evaluation of gastric acid secretory function. PG is prone to pepsin degradation in the stomach, therefore PG is considered inactive when administered orally. Indeed, no effect on acid secretion was noted in four normal subjects subjected to oral administration of PG, whereas some effect was noted in three additional patients with gastrointestinal abnormalities (Morrell & Keynes Lancet. 1975 Oct. 11; 2(7937):712). These findings suggested that the absorption of PG occurred through the injured duodenal mucosa, whereas there was no absorption from the stomach. In fact, this study was cited in a pharmacology textbook as a proof for lack of oral absorption of PG (*Martindale Thirty-second edition*, p1616, the Chapter: "*Supplementary Drugs and Other Substances*"). Furthermore, in vitro studies in which a bullfrog model was used, suggested that PG did not affect the gastric mucosa when applied to the luminal surface (Ayalon A. et al., 1981 The Am. J. Surg. 141:94-97).

WO 01/22985 describes the use of systemic PG in conjunction with a PPI to inhibit gastric acid secretion or as a diuretic. According to this publication, the combined administration of PG and a PPI increases the efficacy of the PPI in reducing/mitigating excess gastric acid secretion. This publication mentions that the combined PG/PPI protocol may be used in the treatment of *H. pylori* infections by enhancing the bioavailability of antibiotics used to treat *H. pylori* infection. It is neither disclosed nor suggested in WO 01/22985 that PG may be active in the stomach when administered orally.

The development of effective treatment for *Helicobacter* sp infections such as *H. pylori* infections would fulfill a long felt need. None of the prior art publications suggest or disclose that PG administered orally in combination with a PPI is effective in treating *H. pylori*-associated disorders.

SUMMARY OF THE INVENTION

It is the object of the present invention to provide novel methods of treating pathological conditions associated with *Helicobacter* sp infections, specifically *H. pylori* infections as well as other pathological conditions in which inhibition of gastric acid secretion is required. In particular, the present invention pertains to the discovery that pentagastrin (PG) administered orally remains stable in the stomach for sufficient time to exert its intra gastric effect. Thus, it is disclosed herein for the first time that PG administered orally possesses a local anti-bacterial effect in the stomach. Furthermore, intra gastric administration of PG in combination with a PPI exhibits a synergistic effect in eradicating *H. pylori* infections. The present discovery is of great importance as it provides the first indication that it is not necessary to apply PG via the parenteral route in order to exert a local effect in the stomach.

In one aspect, the present invention relates to a method of treating a subject suffering from a pathological condition associated with *Helicobacter* sp infection, said method comprises administering to said subject a pharmaceutically effective amount of a peptide comprising the amino acid sequence Trp-Met-Asp-PheNH$_2$ (denoted as SEQ ID NO:1) in conjunction with a proton pump inhibitor (PPI), wherein said peptide is administered orally and remains active in the stomach for sufficient time for exerting its antibacterial effect. A preferred peptide to be used in the method of the present invention is PG which comprises the amino acid sequence βAla-Trp-Met-Asp-PheNH$_2$ (denoted as SEQ ID NO:2). However, this invention contemplates the use of other gastrin or PG analogues or derivatives thereof.

The methods of the present invention involve oral administration of the PG in conjunction with a PPI. The PG can be administered before, simultaneously with, or after the PPI. When the PPI administered is in the delayed enteric-coated form, it is preferable that the PPI administration precedes the PG administration. When the PPI administered is in the immediate non-enteric-coated form, it is preferable that PG administration either precedes the PPI administration or is coadministered with the PPI in order to ensure that the PPI acting locally in the stomach will exert its antibacterial effect together with PG.

In addition to PG which comprises the amino acid sequence βAla-Trp-Met-Asp-PheNH$_2$ (denoted as SEQ ID NO:2), this invention contemplates the use of gastrin or PG analogues or derivatives thereof. Such analogues or derivatives are well known to those of skill in the art. Such variants include, but are not limited to the 34-, 17-, and 14-amino acid species of gastrin, and other peptides including variants such as caerulein. These truncation variants comprise the active C-terminal tetrapeptide Trp-Met-Asp-PheNH$_2$ denoted as SEQ ID NO:1 which is reported in the literature to have full pharmacological activity (see Tracey and Gregory (1964) Nature (London), 204: 935).

Also included are variants of gastrin and/or truncated gastrins where native amino acids are replaced with conservative substitutions. Also included are various analogues of these molecules, including for example, but not limited to the N-protected derivative of PG Boc-βAla-Trp-Met-Asp-PheNH$_2$ in which Boc is tert-butyloxycarbonyl group or F-Moc-βAla-Trp-Met-Asp-PheNH$_2$ in which Moc is methoxycarbonyl.

In addition, it is noted that gastrins are structurally related to the cholecystokinin (CCK) molecules, structurally-related neuropeptides which exist in gastrointestinal tissue and in the CNS (see Mutt V., Gastrointestinal Hormones, Glass G. B. J., [ED.,] Raven Press, N. Y., p 169 and Nisson G., ibid, 127). Thus it is believed that CCKs or analogues or derivatives thereof will be useful in the methods of this invention.

In one embodiment, this invention provides methods of treating pathological conditions associated with *H. pylori* infection in a mammal such as a rodent, bovine, horses, canine, equine, non-human primate or human.

The methods of this invention are not limited to the use of a single PG/analogue or to the use of a single PPI. In certain embodiments, combinations of two or more PPIs and/or two or more PG or analogs thereof are contemplated.

In certain embodiments, it is desirable to administer one or more antibiotics in conjunction with the PPI and PG. Thus, for example, the treatment of ulcers associated with *Helicobacter* sp infection (e. g. *Helicobacter pylori*), the antibiotic will mitigate/eliminate the bacterial component of the pathology.

*H. pylori* is a microaerophilic gram-negative bacterium that is associated with multiple gastrointestinal pathologies, such as gastric peptic ulcer, duodenal peptic ulcer, gastritis, duodenitis, non-ulcer dyspepsia and gastric carcinoma. Thus, the combination of the present invention may be used for prevention and treatment of any gastrointestinal pathology associated with *H. pylori*. Since in a majority of cases, gastric peptic ulcer is considered to be the result of bacterial infection by *H. pylori*, the combination of the present invention may be used for prevention and treatment of any gastrointestinal pathology associated with clinical complaints associated with gastric acid secretion, e.g. in patients on nonsteroidal anti-inflammatory drugs (NSAID) therapy (including low dose aspirin), in patients with Non Ulcer Dyspepsia, in patients with symptomatic gastro-esophageal reflux disease (GERD), in patients with acute upper gastrointestinal bleeding, and in conditions of stress ulceration. Further, the combination of the present invention may be used for treating conditions such as Zollinger-Ellison syndrome (ZES), Werner's syndrome, and systemic mastocytosis.

The present invention further relates to novel oral compositions comprising PG and a PPI. The oral compositions may further comprise an antibiotic. Such oral dosage forms may contain one or both of the drugs in immediate or sustained release form. The oral dosage forms may be in the form of tablets, capsules, troches, lozenges, aqueous or oily suspensions, dispersible powders or granules, emulsions, multiparticulate formulations, syrups, elixirs, and the like.

According to one embodiment, the oral compositions comprising PG and PPI in a single oral dosage form, preferably double-layered solid or semi-solid tablets or hard gelatin capsules. The oral compositions comprising PG and a PPI in a single oral dosage form may further comprise an antibiotic. A preferred dosage form according to the present invention is a capsule containing beads of Omeprazole and PG, each of them with its own characteristic protecting layers and non-active ingredients. Another preferred dosage form according to the present invention is a tablet comprising entericoated Omeprazole in the core and PG in an immediate release-type coating layer.

According to another embodiment, the oral compositions comprising PG, a PPI and possibly an antibiotic are in a separate oral dosage form. For example, PG may be administered in an oral suspension and the PPI and the antibiotic may be administered in a tablet or a capsule. In another example, PG, the PPI and the antibiotic are administered in a tablet or a capsule. According to various embodiments of the present invention, the PPI may be administered in enteric-coated form or non-enteric-coated form.

According to various embodiments, the oral composition further comprises excipients such as a filler, a lubricant, an agent for enhancing bio-adhesion of PG in the stomach, a buffering agent and a solubilizer. The intra gastric release of PG may be sustained by controlled release means, preferably gastro retentive agents. In another embodiment, the intra gastric release of PG is immediate and optionally includes a protease inhibitor.

According to a preferred embodiment, the PPI used in the present invention is enteric-coated in order to prevent its degradation in the stomach. When the PPI is enteric-coated, the PPI granules will be absorbed only when reaching the intestinal environment. According to another embodiment, the PPI used in the present invention is non-enteric-coated in order to permit its immediate action on the gastric $H^+/K^+$-ATPase pumps. Other embodiments include both enteric-coated and non-enteric-coated PPI administered with PG.

These and further embodiments will be apparent from the detailed description and examples that follow.

DETAILED DESCRIPTION OF THE INVENTION

Figure 1:
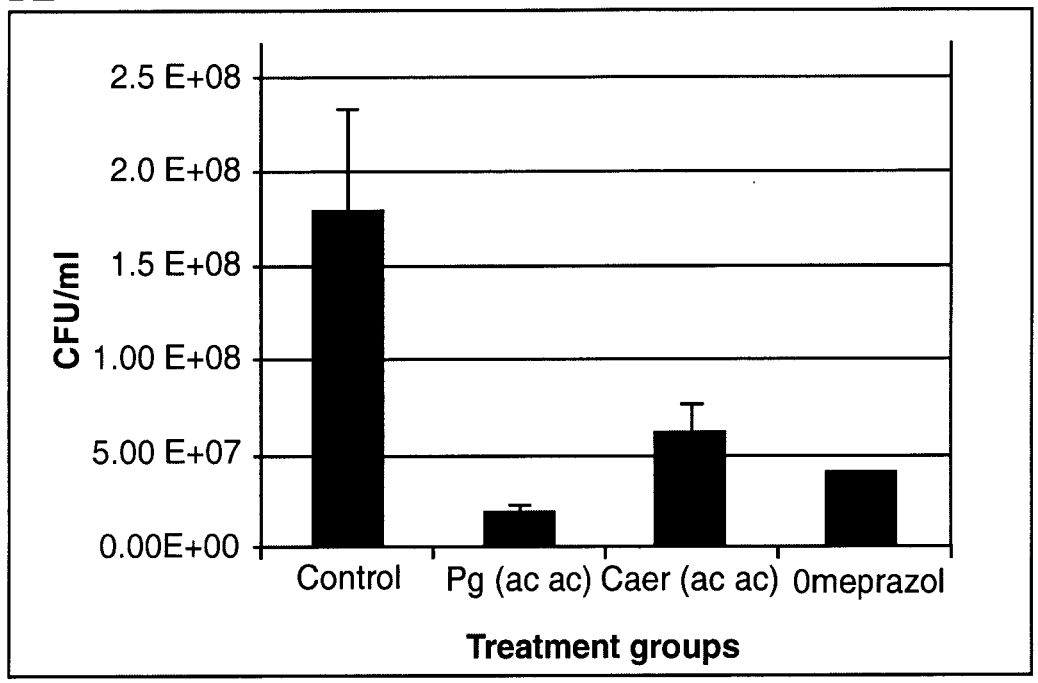
FIGS. 1A and 1B show the effect of PG, caerulein, or omeprazole on bacterial growth in vitro following 48 hours (A) or 5 hours (B) incubation. The viability of the bacteria was assessed using CFU counts.
Figure 1:
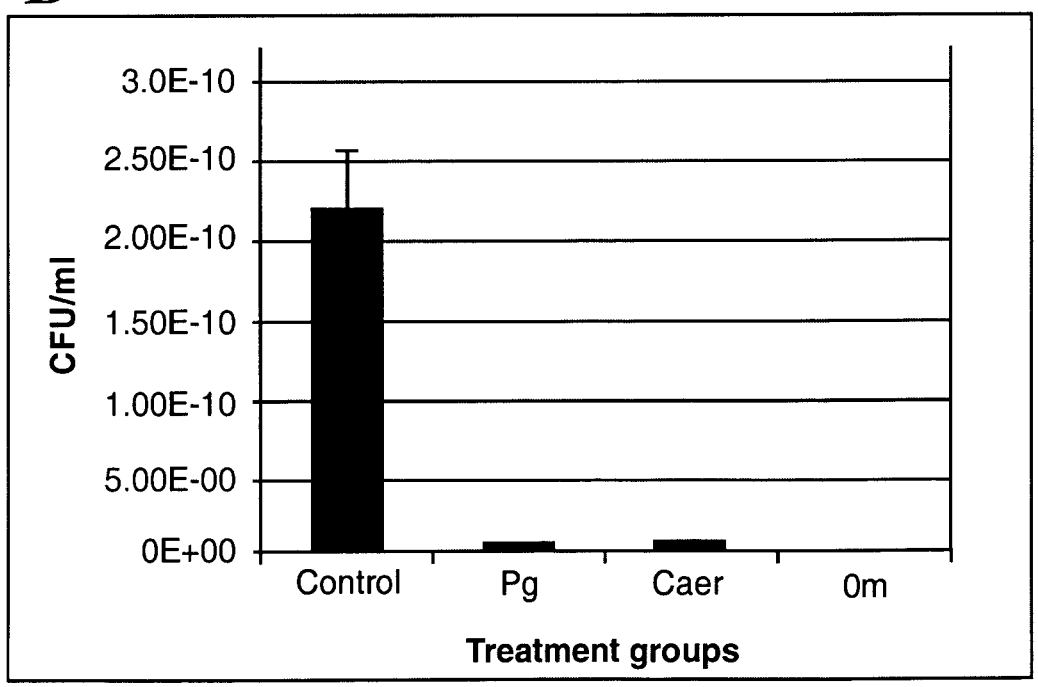

The present invention discloses for the first time that it is not necessary to apply PG via the parenteral route in order to exert a local effect of PG in the stomach. Accordingly, PG administered orally in conjunction with a PPI such as omeprazole exhibits a synergistic effect in eradicating *H. pylori* infections and in treating other gastrointestinal pathological conditions in which inhibition of gastric acid secretion is required.

As demonstrated in the Examples, PG is capable of efficiently eradicating *H. pylori* in vitro. Furthermore, the combination of PG with a PPI such as Omeprazole revealed a synergistic effect on bacterial eradication in vitro. The local activity of PG in the stomach following oral administration was examined both in vitro and in vivo. According to the in vitro experiments, a significant portion of non-degraded PG is left after 15 min of incubation with pepsin in the acidic pH normally present in the stomach. Furthermore, at pH>4.5 which is within the pH range of gastric fluids under PPI treatment, the kinetic of degradation of PG is much longer, leaving a window for its biological activity in the stomach. The in vivo experiments confirmed the in vitro results and revealed that PG administered orally in conjunction with a PPI such as omeprazole is synergistic with the effect of PPI in reducing gastric acid secretion. Furthermore, the in vivo experiments revealed that PG acts on the gastric wall from its luminal side, and not via its absorption into the blood stream through the small bowel mucosa. Therefore, PG administered orally in combination with a PPI is capable of exerting a local effect in the stomach. The local gastric effect of PG involves the eradication of *H. pylori* in the stomach and reduction of gastric acid secretion.

As disclosed herein, PG is administered orally in conjunction with a PPI. When using the term "in conjunction with" it is meant that the PPI and the PG are administered so that there is at least some chronological overlap in their physiological activity on the organism. Thus the PPI and PG can be administered simultaneously and/or sequentially.

The PG can be administered before, simultaneously with, or after the PPI. When the PPI administered is in the delayed enteric-coated form, it is preferable that the PPI administration precedes the PG administration in order to ensure that the PPI absorbed in the intestine will be bioavailable while PG is still active in the stomach. When the PPI administered is in the immediate non-enteric-coated form, it is preferable that PG administration precedes or is coadministered with the PPI in order to ensure that the PPI acting locally in the stomach will act in synergy with PG in eradicating the bacteria.

Thus, in sequential administration, there may be some substantial delay (e.g., minutes or even few hours) between the administration of PG and the PPI as long as the PG has exerted some physiological alteration on the organism when the PPI is administered or becomes active in the organism.

According to a preferred embodiment, the present invention relates to PG which comprises the amino acid sequence βAla-Trp-Met-Asp-PheNH$_2$ (denoted as SEQ ID NO:2). However, other gastrin or PG analogues or derivatives thereof are within the scope of the present invention. Such analogues or derivatives are well known to those of skill in the art. Such variants include, but are not limited to the 34-, 17-, and 14-amino acid species of gastrin, and other truncation variants comprising the active C-terminal tetrapeptide Trp-Met-Asp-PheNH$_2$ denoted as SEQ ID NO:1 which is reported in the literature to have full pharmacological activity (see Tracey and Gregory (1964) Nature (London), 204: 935).

Also included are variants of gastrin and/or truncated gastrins where native amino acids are replaced with conservative substitutions. Also included are various analogues of these molecules, including for example, but not limited to the N-protected derivatives of PG. Suitable protecting groups for PG include standard hydroxyl protecting groups known in the art, e.g., methoxymethyl (MOM), β-methoxyethoxymethyl (MEM), trialkylsilyl, triphenylmethyl (trityl), tert-butoxycarbonyl (t-BOC), ethoxyethyl (EE), f-MOC (methoxycarbonyl), TROC, etc. The protecting group(s) may be removed by using standard procedures which are generally known to those skilled in the art to give the desired PG derivatives (T. W. Green, Protective Groups in Organic Synthesis, Chapter 2, pages 10-69 (1981)).

In addition, it is noted that gastrins are structurally related to CCK neuropeptides which exist in gastrointestinal tract and in the CNS (see Mutt V., Gastrointestinal Hormones, Glass G. B. J., [ED.,] Raven Press, N.Y., p 169 and Nisson G., ibid, 127). Thus it is believed that CCK or analogues or derivatives thereof that stimulate endogenous gastrin secretion will be useful in the methods of this invention.

Gastrins, pentagastrins, or analogues are commercially available. In addition, synthetic protocols are well known. Thus, for example, PG can be chemically synthesized using well known peptide synthesis methodologies (see, e.g. Barany and Merrifield Solid-Phase Peptide Synthesis; pp. 3-284 in The Peptides: Analysis, Synthesis, Biology. Vol. 2: Special methods in peptide synthesis, part a.; Merrifield et al. (1963) J. Am. Chem. Soc., 85: 2149-2156; and Stewart et al. (1984) Solid Phase Peptide Synthesis, 2nd ed. Pierce Chem. Co., Rockford, Ill.). Additionally, PG can be chemically synthesized by conjugation of a Boc-Ala residue to the tetrapeptide Trp-Met-Asp-PheNH$_2$.

Numerous proton pump inhibitors are known to those of skill in the art. Thus, for example, U.S. Pat. No. 6,093,738 describes novel thiadiazole compounds that are effective as proton pumps inhibitors. European Patent Nos. 322133 and 404322 disclose quinazoline derivatives, European Patent No. 259174 describes quinoline derivatives, and WO 91/13337 and U.S. Pat. No. 5,750,531 disclose pyrimidine derivatives, as proton pump inhibitors. Suitable proton pump inhibitors are also disclosed for example in EP-A1-174726, EP-A1-166287, GB 2 163 747 and WO 90/06925, WO 91/19711, WO 91/19712, WO 94/27988 and WO 95/01977. In general, any proton pump inhibitor which is activated within the acid canaliculi and inhibits the activity of the H$^+$/K$^+$-adenosine triphosphatase (ATPase) proton pump may be used in combination with PG. Particularly preferred PPIs include, but are not limited to omeprazole, rabeprazole, lansoprazole, and pantoprazole and derivatives or analogues thereof.

The PPIs used in the dosage forms of the invention can be used in neutral form or in the form of a salt (e.g., an alkaline salt), such as for instance the Mg$^{+2}$, CA$^{+2}$, NA$^+$, K$^+$, or Li$^+$ salts, preferably the Mg$^{+2}$ salts. Further where applicable, the compounds can be used in racemic form or in the form of an enantiomer thereof, or salts of the racemates or the single enantiomers.

The present invention further relates to novel oral compositions comprising PG, a PPI and pharmaceutically acceptable carrier. The oral compositions may further comprise an antibiotic for the treatment of ulcers associated with *Helicobacter* sp infection (e.g. *Helicobacter pylori*). Such antibiotics are for example amoxicillin, clarithromycin or other macrolides, metronidazole and related antibiotics, tetracycline, quinolones, rifabutin or furazolidone. Optionally, the composition can further comprise a protease inhibitor.

In preferred embodiments of the present invention, the pharmaceutical compositions containing the proton pump inhibitors and the PG are administered orally. Such oral dosage forms may contain one or both of the drugs in immediate or sustained release form. The oral dosage forms may be in the form of tablets, capsules, troches, lozenges, aqueous or oily suspensions, dispersible powders or granules, emulsions, multiparticulate formulations, syrups, elixirs, and the like.

Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They can also be combined where desired with other active agents, e.g., antibiotics. For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

According to one embodiment, the oral compositions comprising PG and PPI in a single oral dosage form, preferably double-layered tablets or hard gelatin capsules. The oral compositions comprising PG and a PPI in a single oral dosage form may further comprise an antibiotic. A preferred dosage form according to the present invention is a capsule containing beads of omeprazole and PG, each of them with its on characteristic protecting layers and non-active ingredients.

According to another embodiment, the oral compositions comprising PG, a PPI and possibly an antibiotic are in a separate oral dosage form. For example, according to one preferred embodiment, PG is administered in an oral solution and the PPI and the antibiotic may be administered in a tablet or a capsule (hard gelatin capsule or soft Gelatin capsule) According to another preferred embodiment, PG, the PPI and the antibiotic are administered in a tablet or a capsule (hard gelatin capsule or soft Gelatin capsule). When the active ingredient is formulated in a tablet or a capsule, it is desirable to incorporate bio-adhesive agents in order to enhance the bio-adhesion of PG. For example, PG may be granulated or microspheres may be prepared with bioadhesive polymers such as Carbopol, Eudragit® (methacrylic copolymer), CMC, Chitosan derivatives, Dextran derivatives or Polyox.

According to various embodiments, the PPIs used in the present invention may be absorbed in the intestine when using the enteric-coated form. Alternatively, the PPIs may be in the uncoated form, in which it acts directly on the stomach wall lumen. According to a preferred embodiment, the PPI granules used in the present invention are enteric-coated in order to prevent its degradation in the stomach for example by using Eudragit. In this case, the coated PPI granules will be instantly degraded when reaching the intestinal environment at pH 5 and higher.

Examples of suitable enteric polymers include cellulose acetate phthalate, hydroxypropylnethylcellulose phthalate, polyvinylacetate phthalate, methacrylic acid copolymer, shellac, hydroxypropylmethylcellulose succinate, cellulose acetate trimellitate, and mixtures of any of the foregoing. A suitable commercially available enteric material, for example is sold under the trademark Eudragit.TM. L 100-555, as defined above. This coating can be spray coated onto the substrate as previously mentioned with respect to the other layers of this embodiment of the invention. Preferably, the coating to prevent contact of said proton pump inhibitor with acidic gastric juice is applied directly over the proton pump inhibitor without an intermediate separating layer.

According to one embodiment, a single dosage form comprising PG, a PPI and optionally an antibiotic is prepared in the form of a hard gelatin capsule. In one example, an antibiotic such as amoxicillin, PG and omeprazole are filled into hard gelatin capsules. The hard gelatin capsules further comprise a filler such as microcrystalline cellulose known as Avicel®, a lubricant, an agent for enhancing bio-adhesion of PG, and a solubilizer.

Preferred lubricants for hard gelatin capsules are for example magnesium stearate, Stearic acid, lactos, diCalcium Phosphate, colodial silica and Talc. Preferred solubilizers for hard gelatin capsules are for example Tween 80, Vitamin E TPGS, starch and Croscarmellose sodium.

According to another embodiment, a single dosage form comprising PG, a PPI and optionally an antibiotic is prepared in the form of a tablet. In one example, amoxicillin (or another antibiotic), pentagastrin and omeprazole are filled into double layer tablets. According to a preferred embodiment, the first layer comprises amoxicillin granulated together with PG preferably in the presence of a bioadhesive polymer such as carbopol 971P and lactose. The second layer comprises omeprazole granulated with an enteric polymer such as Eudragit.

Aqueous suspensions containing the above-identified combination of drugs and that mixture have one or more excipients suitable as suspending agents, for example pharmaceutically acceptable synthetic gums such as hydroxypropylmethylcellulose or natural gums. Oily suspensions may be formulated by suspending the above-identified combination of drugs in a vegetable oil or mineral oil. The oily suspensions may contain a thickening agent such as beeswax or cetyl alcohol. A syrup, elixir, or the like can be used wherein a sweetened vehicle is employed.

In formulations prepared using multiparticulate substrates comprising enterically coated proton pump inhibitor, such multiparticulates may be mixed with PG (e.g., in particulate or powder form) and then separated into unit doses. Alternatively, the enterically coated substrates containing the proton pump inhibitor may thereafter by coated with the PG (with or without further optional overcoatings). Alternatively, two separate populations of substrates may be used, one population of substrates being coated with the proton pump inhibitor and thereafter enteric-coated, the other population of substrates comprising the PG. The PG-containing substrates may comprise inert beads coated with the PG, or may comprise a plurality of immediate release matrices containing the PG. Thereafter, requisite amounts of each of the two populations of substrates could be incorporated into tablets, or into gelatin capsules, for example.

In embodiments where the substrates comprise inert pharmaceutically acceptable beads, the drug(s) may be mixed with further ingredients prior to being coated onto the beads. Ingredients include, but are not limited to, binders, surfactants, fillers, disintegrating agents, alkaline additives or other pharmaceutically acceptable ingredients, alone or in mixtures. Binders include, for example, celluloses such as hydroxypropyl methylcellulose, hydroxypropyl cellulose and carboxymethyl-cellulose sodium, polyvinyl pyrrolidone, sugars, starches and other pharmaceutically acceptable substances with cohesive properties. Suitable surfactants include pharmaceutically acceptable non-ionic or ionic surfactants. An example of a suitable surfactant is sodium lauryl sulfate. The inert beads may be first coated with the proton pump inhibitor, overcoated with an enteric coating, and thereafter coated with the PG (with or without further optional overcoatings). Alternatively, two separate populations of beads may be used, one population of beads being coated with the proton pump inhibitor and thereafter enteric-coated, the other population of beads being coating with the PG. Thereafter, requisite amounts of each of the two populations of beads could be incorporated into tablets, or into gelatin capsules, for example.

Alternatively, the proton pump inhibitor may be optionally mixed with alkaline compounds and further mixed with suitable ingredients (with or without the PG) as set forth above and then formulated into the substrate. Such substrates may be manufactured via extrusion/spheronization, balling or compression utilizing different process equipments. The size of the substrates maybe, for example, from about 0.1 to about 4 mm, and preferably from about 0.1 to about 2 mm. Alternatively, the substrates may include additional ingredients. Such suitable ingredients include fillers, binders, lubricants, disintegrating agents, surfactants and other pharmaceutically acceptable additives. The alkaline compound may be selected from substances such as the sodium, potassium, calcium, magnesium and aluminium salts of phosphoric acid, carbonic acid, citric acid or other suitable weak inorganic or organic acids; aluminium hydroxide/sodium bicarbonate coprecipitate; substances normally used in antacid preparations such as aluminum, calcium and magnesium hydroxides; magnesium oxide or composite substances; organic pH-buffering agents such as trihydroxymethylaminomethane, basic amino acids and their salts or other similar, pharmaceutically acceptable pH-buffering substances. Alternatively, the aforementioned substrate can be prepared by using spray drying or spray congealing technique.

The proton pump inhibitor omeprazole has an asymmetric center in the sulfur atom, i.e. exists as two optical isomers (enantiomers). Both the pure enantiomers, racemic mixtures (50% of each enantiomer) and unequal mixtures of the two enantiomers are suitable for the pharmaceutical formulation according to the present invention. A suitable form of omeprazole for preparation of multiparticulate dosage forms in accordance with the invention can be the magnesium salt of omeprazole with a specific degree of crystallinity and other physical properties disclosed in WO 95/01977, hereby incorporated by reference. Other suitable forms of the active substance are the sodium, potassium, magnesium and calcium salts of the single enantiomers of omeprazole, especially in their crystalline form described in WO 94/27988, hereby incorporated by reference.

Before applying enteric coating layer(s) onto the substrate, the substrates may optionally be covered with one or more separating (intermediate) layers, however, in preferred embodiments, the enteric coating is applied directly onto the proton pump inhibitor without the need for a separating layer.

Preferably, one or more enteric coating layers are applied onto the substrate using a suitable coating technique. The enteric coating layer material may be dispersed or dissolved in either water or in suitable organic solvents. As enteric coating layer polymers one or more, separately or in combination, of the following can be used; e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s).

The enteric coating layers preferably contain effective amounts of pharmaceutically acceptable plasticizers to obtain the desired mechanical properties, such as flexibility and hardness of the enteric coating layers. Such plasticizers are for instance, but not restricted to, triacetin, citric acid esters, phthalic acid esters, dibutyl sebacate, cetyl alcohol, polyethylene glycols, polysorbates or other plasticizers. The amount of plasticizer is optimized for the particular situation. The amount of plasticizer is usually above 10% by weight of the enteric coating layer polymer(s), preferably 15-50%, and more preferably 20-50%. Additives such as dispersants, colorants, pigments, polymers e.g. poly(ethylacrylate, methylmethacrylate), anti-tacking and anti-foaming agents may also be included into the enteric coating layer(s). Other compounds may be added to increase film thickness and to decrease diffusion of acidic gastric juices into the add susceptible material.

Overcoatings may be applied to the substrates coated as set forth above, e.g., by coating or layering procedures in suitable equipments such as coating pan, coating granulator or in a fluidized bed apparatus using water and/or organic solvents for the coating or layering process. Suitable overcoating materials include sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium and the like. Additives such as plasticizers, colorants, pigments, fillers, anti-tacking and anti-static agents, such as for instance magnesium stearate, titanium dioxide, talc and other additives may also be included into the over-coating layer(s).

The enteric coated substrates may then be mixed with tablet excipients and compressed into a multiple unit tableted dosage form according to the present invention, or alternatively incorporated as unit doses in appropriately sized gelatin capsules. Compressed, tablets prepared in accordance with the invention are optionally covered with a film-formiing agent(s) to obtain a smooth surface of the tablet and further enhance the stability of the tablet during packaging and transport. Such a tablet coating layer may further comprise additives like anti-tacking agents, colorants and pigments or other additives to obtain a tablet of good appearance. The compaction process (compression) for formulating the multiple unit tableted dosage form must not significantly affect the acid resistance of the enteric coated substrates. In other words the mechanical properties, such as the flexibility and hardness as well as the thickness, of the enteric coating layer(s) must secure that the requirements on enteric coated articles in the United States Pharmacopeia are accomplished and that the acid resistance does not decrease more than 10% during the compression of pellets into tablets.

In certain preferred embodiments, where the PG is incorporated into the formulation after the enteric coating of the proton pump inhibitor substrates, the addition of the PG after the addition of the enteric coating to the substrates allows for rapid release of the PG and delayed release of proton pump inhibitor. The PG may be present in an outer coating in a form that does not retard its release, or may be separately incorporated into the formulation as set forth above.

Optionally soft gelatin capsules can be manufactured by filling a composition comprising the active ingredients as mentioned above and a known vegetable oil into capsules. Hard gelatin capsules can also be manufactured by filling into capsules the tablet, granules or pellets, each comprising an active ingredient as mentioned above, and a solid particulate carrier such as lactose, sucrose, sorbitol, mannitol, potato starch, corn starch, amylopectin, a cellulose derivative or gelatin.

Formulations according to the invention that utilize pH-dependent coatings to obtain formulations may also impart a repeat-action effect whereby unprotected drug, preferably the PG, is coated over the enteric coat and is released in the stomach, while the remainder, preferably containing the proton pump inhibitor, being protected by the enteric coating, is released further down the gastrointestinal tract. Coatings which are pH-dependent may be used in accordance with the present invention, including shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the proton pump inhibitor and PG is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile.

In addition to the above ingredients, the matrix may also contain suitable quantities of other materials, e.g. diluents, lubricants, binders, granulating aids, colorants, flavorants and glidants that are conventional in the pharmaceutical art. The quantities of these additional materials will be sufficient to provide the desired effect to the desired formulation. Specific examples of pharmaceutically acceptable carriers and excipients that may be used to formulate oral dosage forms are described in the Handbook of Pharmaceutical Excipients, American Pharmaceutical Association (1986), incorporated by reference herein.

A further ingredient which can be added to the matrix is a pH modifying agent which is defined for purposes of the present invention to mean any substance which decreases the ionization of the medicament, whereby the release of the drug from the matrix and into solution is facilitated. Suitable pH modifying agent are organic acids such as citric acid, succinic acid, fumaric acid, malic acid, maleic acid, glutaric acid or lactic acid.

Dosages for typical therapeutics, particularly for PPIs and PG, are well known to those of skill in the art. Moreover, such dosages are typically advisorial in nature and may be adjusted depending on the particular therapeutic context, patient tolerance, etc. Single or multiple dosages of the compositions may be administered depending on the dose and frequency as required and tolerated by the patient.

In preferred embodiments, the PG and PPI may be administered in an amount sufficient to obtain a measurable effect on the bacteria or on the gastric acid secretion. Specifically, the PG and PPI may be administered in an amount sufficient to effect a significant decrease in gastric acid secretion (e.g., a statistically significant decrease at the 90%, more preferably at the 95%, and most preferably at the 98% or 99% confidence level).

Similarly, where the PG and PPI are administered in combination with an antibiotic, the antibiotic is typically administered in a manner and concentration consisting with clinical practice.

Preferred dosages for omeprazole are between 10-40 mg/day, lansoprazole is typically administered about 15-30 mg/day; rabeprazole is typically administered 20 mg/day and pantoprazole is typically administered 40 mg/day. However, any therapeutic or sub-therapeutic dose of these agents is considered within the scope of the present invention. Preferred dosages for PG administered orally are between 2.5-20 mg/day, preferably 5 mg/day.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Methods and Reagents:

The peptides used in this study included either pentagastrin (PG) or caerulein (Sigma, St. Louis, Mo., USA). Peptides were diluted as a stock solution into acetic acid/water (1:1) at a concentration of 1 mg/ml, after which they were diluted to the final concentration, either in water or directly into the culture medium. In some experiments, PG was diluted in acetic acid/water 1:1 and 2.5% DMSO (Sigma). Omeprazole (Dexxon, Or Akiva, Israel) was diluted in PBS with 2.5% DMSO, and used at 32 µg/ml.

The bacterial strains that were used included *H. pylori* strain J.99 or H-88 (a clinical isolate), and were grown on chocolate agar plates (Remel Novamed, Jerusalem, Israel). Bacteria were thawed and grown for two days under microaerophilic conditions using a gas generating kit (AnaeroPack system, Mitsubishi gas chemical company, NY, N.Y., USA). Following culture, a second passage was performed under similar conditions, and the bacteria were grown for one additional day. For experimentation, bacteria were diluted in PBS, after which 0.02 $OD_{600}$ of second passage bacteria (>80% bacillary form) were transferred into Brucella (Becton Dickinson, Cockesville, Md., USA) or Brain heart (Biolife, Milano, Italy) broth containing 0.5-2% inactivated human serum containing the appropriate peptides in 25 $cm^2$ tissue culture flasks (Nunc, Rosklide, Denmark). Bacteria were grown for up to 48 hours. All cultures were performed at 37° C. Growth was assessed using $OD_{600}$ measurements or CFU counts. In other experiments, second passage bacteria were washed in PBS, after which 0.5 OD (final concentration) were re-suspended in F12 HAM medium (Biological industries, Beit Haemek, Israel) in 24-well plates (TPP, Switzerland). Bacteria were incubated for five hours in the presence of PG or caerulein. The effect of the peptides on bacterial growth was assessed by CFU quantitation. The viability of the bacteria as assessed by the cellTiter 96 Aqueous cell proliferation assay (Promega, Madison Wis., USA).

Example 1

Inhibition of Bacterial Growth with PG, Caerulein or Omeprazole.

In preliminary experiments, the effect of PG, caerulein, and omeprazole on the growth of *H. pylori* was established. In this experiment, *H. pylori* (H-88 clinical isolate) were grown in liquid medium containing PG and caerulein diluted in acetic acid. In parallel, the effect of omeprazole on bacterial growth was also assessed. Untreated bacteria served as controls. Bacterial growth was assessed using CFU counts. As can be seen in FIG. 1A, both peptides inhibited bacterial growth to an extent similar to that of omeprazole during incubation for 48 hours. Additional experiments were performed to assess whether these compounds not only inhibited bacterial proliferation, but also affected bacterial viability during a short-term culture. As can be seen in FIG. 1B, both peptides and omeprazole also had a similar effect during short-term cultures.

Example 2

Pentagastrin and Omeprazole Inhibit Synergistically the Growth of *H. pylori*.

Figure 2:
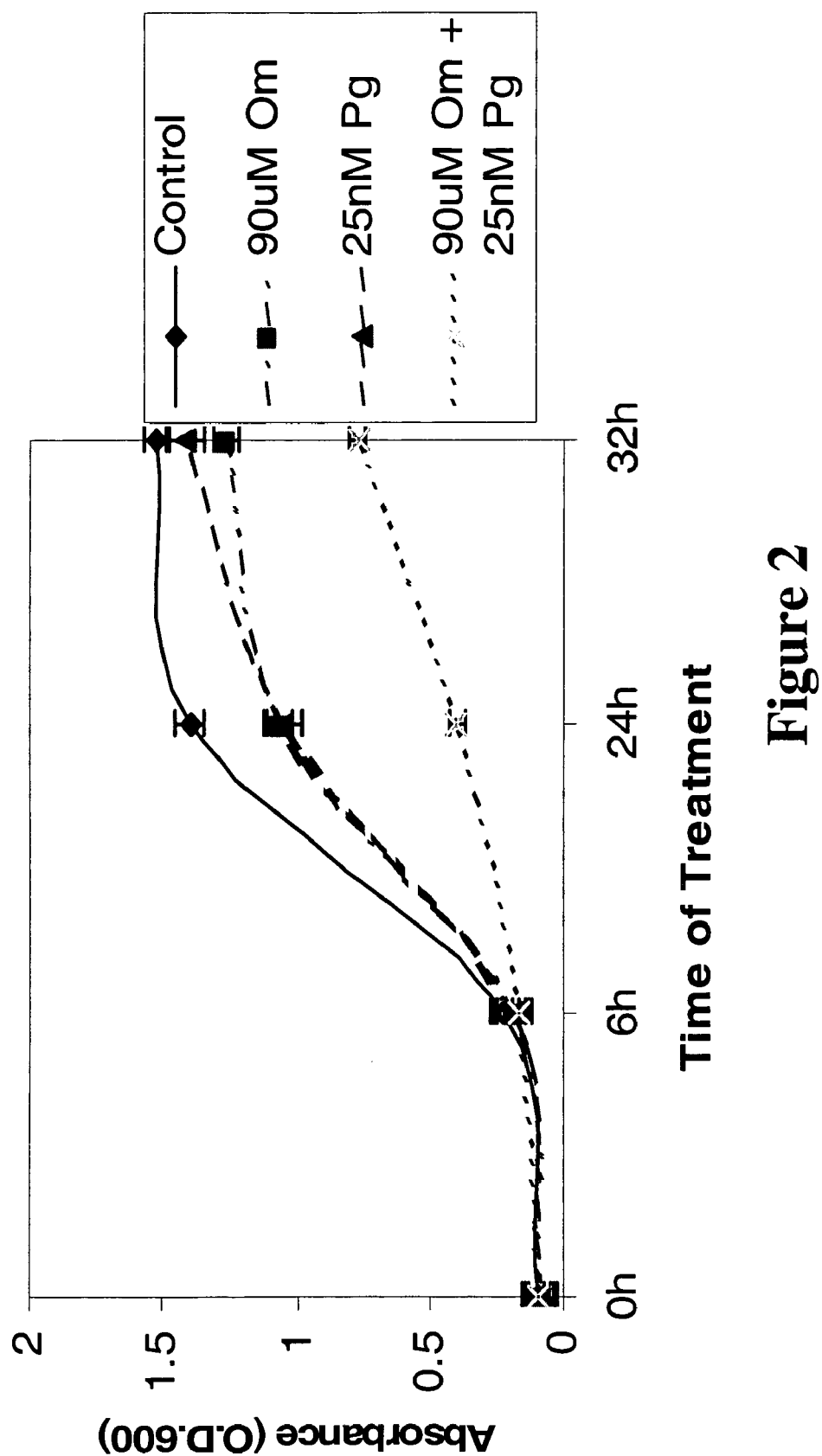
FIG. 2 shows the synergistic effect of PG and omeprazole on bacterial eradication in vitro.

It was previously shown that omeprazole or pentagastrin inhibit growth of *H. pylori* in vitro. In order to investigate the effect of combined administration, the growth of bacteria in the presence of omeprazole, pentagastrin or both was examined. Bacteria were inoculated in 6 ml of Brain heart broth with 1% of human serum and grown at 37° C. for 18 hours in microaerobic conditions. Then, all identically growing cultures were supplemented with either 90 µM omeprazole, or 25 nM pentagastrin, or both and incubated for additional 32 hours. Bacterial culture grown in the absence of chemicals was used as a positive control of bacterial growth. The level of bacterial growth was monitored spectrophotometrically after 6, 24, and 32 hours of treatment. As demonstrated in FIG. 2, single treatment by either omeprazole or pentagastrin showed a moderate inhibition upon bacterial growth. Addition of both agents significantly slowed the growth suggesting that the combination of omeprazole and pentagastrin possesses synergistic inhibitory effect upon growth of *H. pylori*.

Example 3

Pentagastrin, Omeprazole, and Amoxicillin Synergistically Inhibit Growth of *H. pylori*.

In an attempt to optimize the antibacterial formulation for eradication of *H. pylori*, the effect of pentagastrin and omeprazole provided in combination with amoxicillin was tested. Amoxicillin is a commonly accepted antibiotic used for *H. pylori* treatment. To investigate the effect of triple administration we tested the growth of bacteria in the presence of omeprazole, pentagastrin, amoxycillin, and their possible combinations was tested. Bacteria grown in the absence of any agent was used as a negative control. The level of bacterial growth was monitored spectrophotometrically after 18, 24, and 46 hours of treatment.

Figure 3:
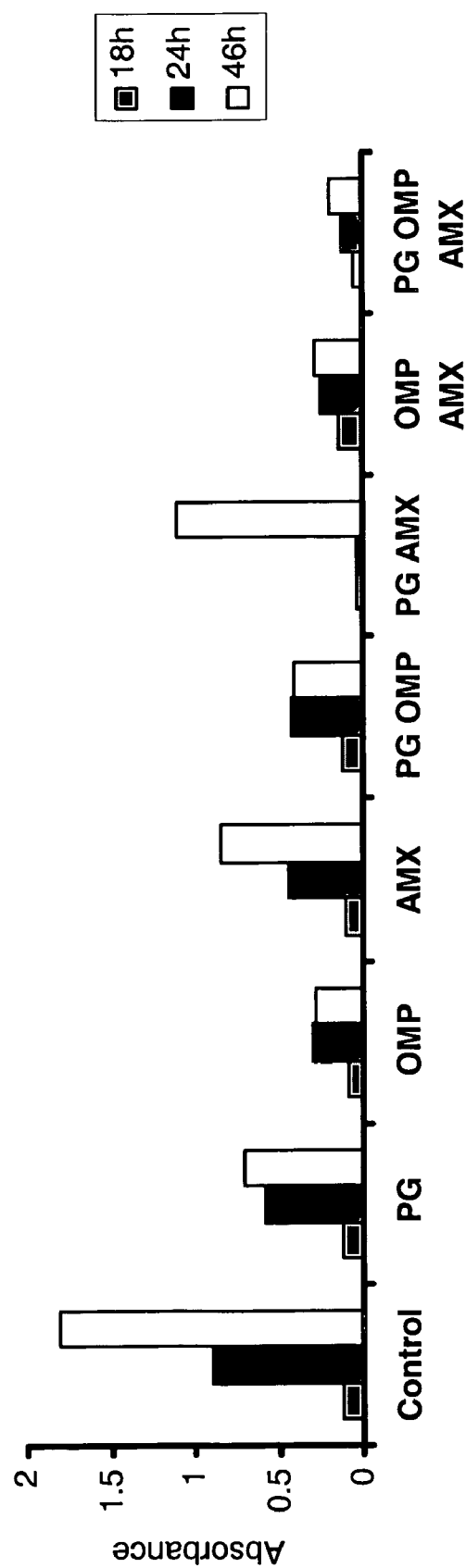
FIG. 3 shows the synergistic effect of PG, omeprazole and amoxycillin on bacterial eradication in vitro.

Single treatment by omeprazole, pentagastrin, or amoxicillin showed a moderate inhibition upon bacterial growth (FIG. 3). Exposure of bacteria to triple-combined treatment revealed the highest level of inhibition. This effect is significantly stronger than that of the single treatments (PG, OMP, or AMX) as well as the double treatments (PG and OMP, PG and AMX, OMP and AMX) (FIG. 3). The present results imply that the treatment formulation that combines pentagastrin, omeprazole, and amoxycillin might be considered as an optimal for eradication of *H. pylori*.

Example 4

Caerulein, and Omeprazole are Effective in the Eradication of *H. pylori*.

*H. pylori* were incubated in the presence of the combinations of omeprazole and PG or caerulein, and the growth of the bacterium was assessed using $OD_{600}$ readings and viability measurements. As can be seen in Table 1, the combination of omeprazole with either agents was highly efficacious for the eradication of the bacterium. The effect of the combination of the drugs was evident after five hours using the metabolic viability assay, indicating that it had a bactericidal effect. A similar effect was noted after incubation of the bacteria with the combination of drugs for 48 hours. These findings indicate that the drug combinations were also effective in inhibiting the growth of the bacterium.

TABLE 1

Effect of Omeprazole and gastrin-analogue combinations on the growth of *H. pylori*.

| | Bacterial Viability $OD_{590}$ 5 hours | Bacterial Turbidity $OD_{600}$ 48 hours |
|---|---|---|
| Control | 1.825 | 1.195 |
| Omeprazole + PG | 0.765 | 0.043 |
| Omeprazole + Caerulein | 0.769 | 0.048 |

Example 5

Combined Formulation of PG and PPI for the Inhibition of Acid Secretion In Vivo.

Reagents and Animals:

The following reagents were used during the experiments: Ketamine HCL (Ketaset, Pfizer GmbH, Karlsruhe, Germany), Medetomidinhydrochloride (Domitor, Pfizer), Lansoprazole (Zoton, CTS Chemical Industries, Kiryat Malachi, Israel), Omeprazole (kindly supplied by Dexxon, Or Akiva, Israel), Pentagastrin for injection (Cambridge Laboratories, GB). Sodium Hydroxide was obtained from Sigma (St. Louis, USA).

Male and female Wistar Hanover rats, 7-10 weeks of age, were obtained from Harlan Laboratories (Rehovot, Israel). Animals were fed standard chow and received unlimited water supply. The animals were kept in automatically controlled temperature (between 20-24° C.), a 12-hour light/dark cycle, and 15 air changes an hour.

Experimental Design:

Rats were fasted (with water freely available) for 24 hours before experimentation. PG or saline were introduced into the stomach by means of a steel feeding needle. Thereafter, the animals were injected with Domitor and Ketaset; the abdominal wall was dissected and gastric fluid (approximately 30 μl) was collected by puncture with a needle (0.45×13 2006-09 Artsana S.P.A., Grandate (CO), Italy) at the indicated time points. Gastric juice was kept frozen at −80° C. until use. In some experiments, the rats were first anesthetized and dissected, after which test reagents were introduced by direct injection into the stomach. In additional experiments, oral introduction of test reagents was performed, after which the abdominal wall was rapidly dissected and the pylorus ligated (using a surgical suture and cutting needle, Dermalon, Sherwood, Davis & Geck, St. Louis, USA). Thereafter, the gastric contents were aspirated as described.

The experiments included animals that received the following treatments:

A. No pylorus ligation:

PG, 50 μg in 200 μl saline, P.O.

PG, 6 μg/Kg in 50 μl saline, S.C.

Saline, 200 μl, P.O.

B. Tests with pylorus ligation:

PG, 50 μg in 200 μl saline, P.O.

Saline, 200 μl, P.O.

In yet other experiments, 7.5 mg of omeprazole or normal saline suspended in propylene glycol were administered by oral gavage as pre-treatments. Thirty minutes later, animals were challenged orally or by direct intragastric injection, according to the following groups:

PG, 50 μg in 200 μl saline, P.O.

PG, 50 μg in 200 μl saline, P.O., and 7.5 mg omeprazole

Finally, an omeprazole dose-response study was performed, in order to find the optimal dose of omeprazole to be combined with pentagastrin in order to allow safe and effective therapy. In this study, animals were fed with different doses of omeprazole (30, 10, and 5 mg/kg) in conjunction with pentagastrin (50 μg/kg, administered by direct intragastric injection).

Measurement of Gastric Juice Acidity:

Frozen gastric juice was defrosted at room temperature, mixed by vortexing, and centrifuged for 5 minutes at 14,000 RPM. Ten μl of the sample were diluted in 40 μl of distilled water. The pH was measured, and NaOH (0.001 N) was added to the sample until pH 7 was reached, as determined by measuring pH using a pH meter (pH211, Hanna Instruments, 35030 Sameola di Rubano, Italy).

Statistics

Data are presented with standard errors. The significance of the results was tested using the Mann Whitney non-parametric test.

A. Oral Introduction of PG

Figure 4:
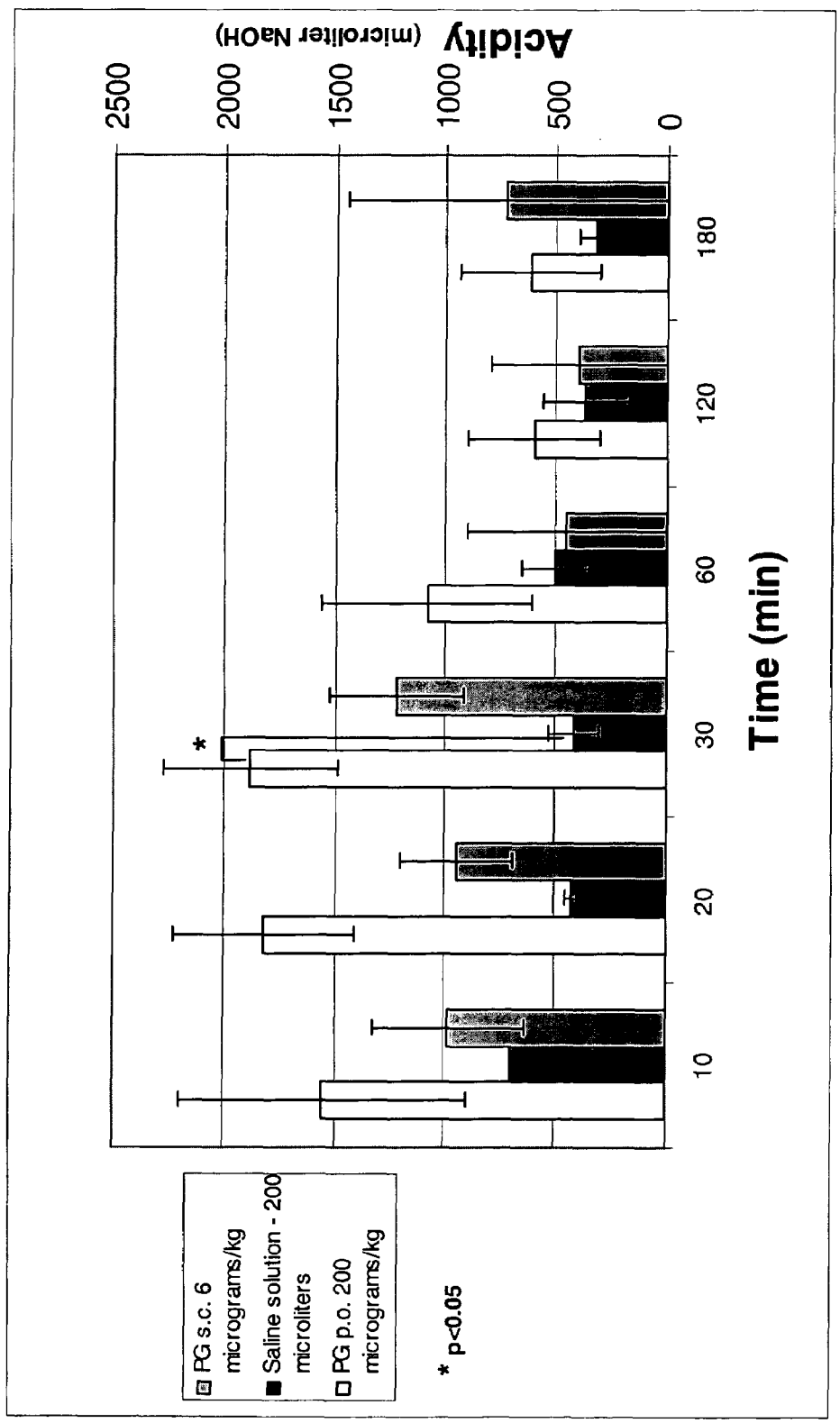
FIG. 4 shows that PG administered orally is effective in inducing gastric acid secretion.

The initial experiments were undertaken to determine the effect of oral introduction of PG to fasted rats. Measurement of acid secretion was used as a surrogate marker for the effect of absorbed PG. As shown in FIG. 4, administration of oral PG resulted in a significant secretion of acid into the gastric lumen. This effect was maximal and significant 30 minutes after oral PG introduction (p=0.05), and remained consistently elevated relative to acidity levels which followed subcutaneous (SC) administration of PG and the neutral, saline-only control for 60 minutes post-exposure. This observation suggested that surprisingly, and in contrast to the previously published information, PG was bioavailable to deeper gastric mucosal layers following oral administration.

Figure 5:
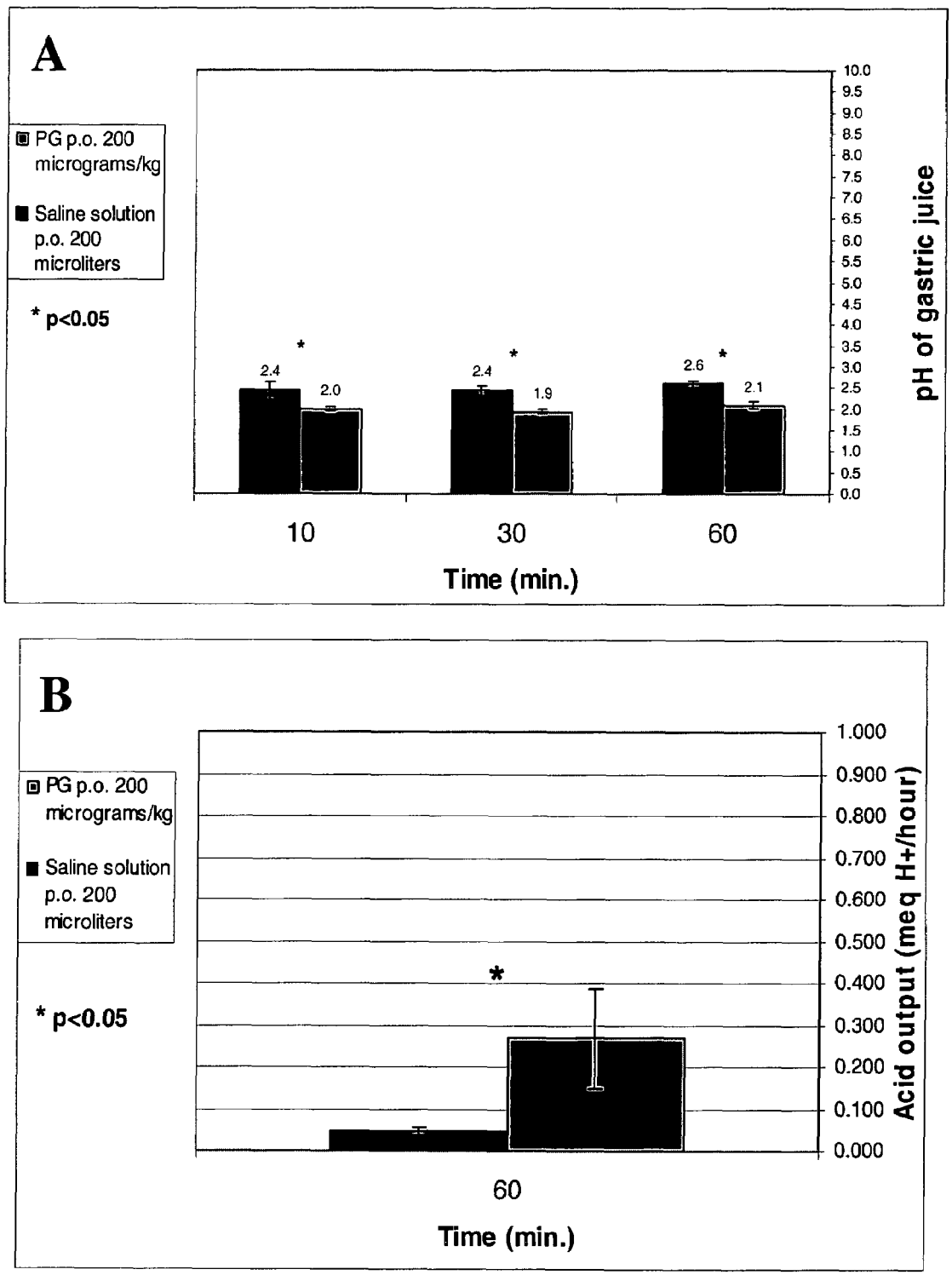
FIGS. 5A and 5B show the acid secretion following oral PG administration to pylorus-ligated rats. The results represent the pH values (A) and gastric acid output ($meqH^+$/hour) (B) obtained following PG oral administration.

The absorption of PG could occur via a number of anatomical sites. Thus, the peptide may be absorbed directly from the stomach. Alternatively, it may reach the gastric mucosal layer via the blood stream following its absorption from the small intestine, which is the site through which most peptides are normally absorbed. To assess whether PG was absorbed from the gastric lumen, its effect on acid secretion was tested following administration to rats in which the pylorus was ligated. As shown in FIGS. 5A and 5B, oral administration of PG into the ligated stomach induced significant secretion of gastric acid: the initial pH decreased and the gastric acid output significantly increased following administration of PG compared with saline at all the tested time points (p<0.05). This observation indicated that PG exerted its effect directly through the gastric lumen, probably by reaching the gastrin/CCK-B receptors within the gastric mucosa.

Figure 6:
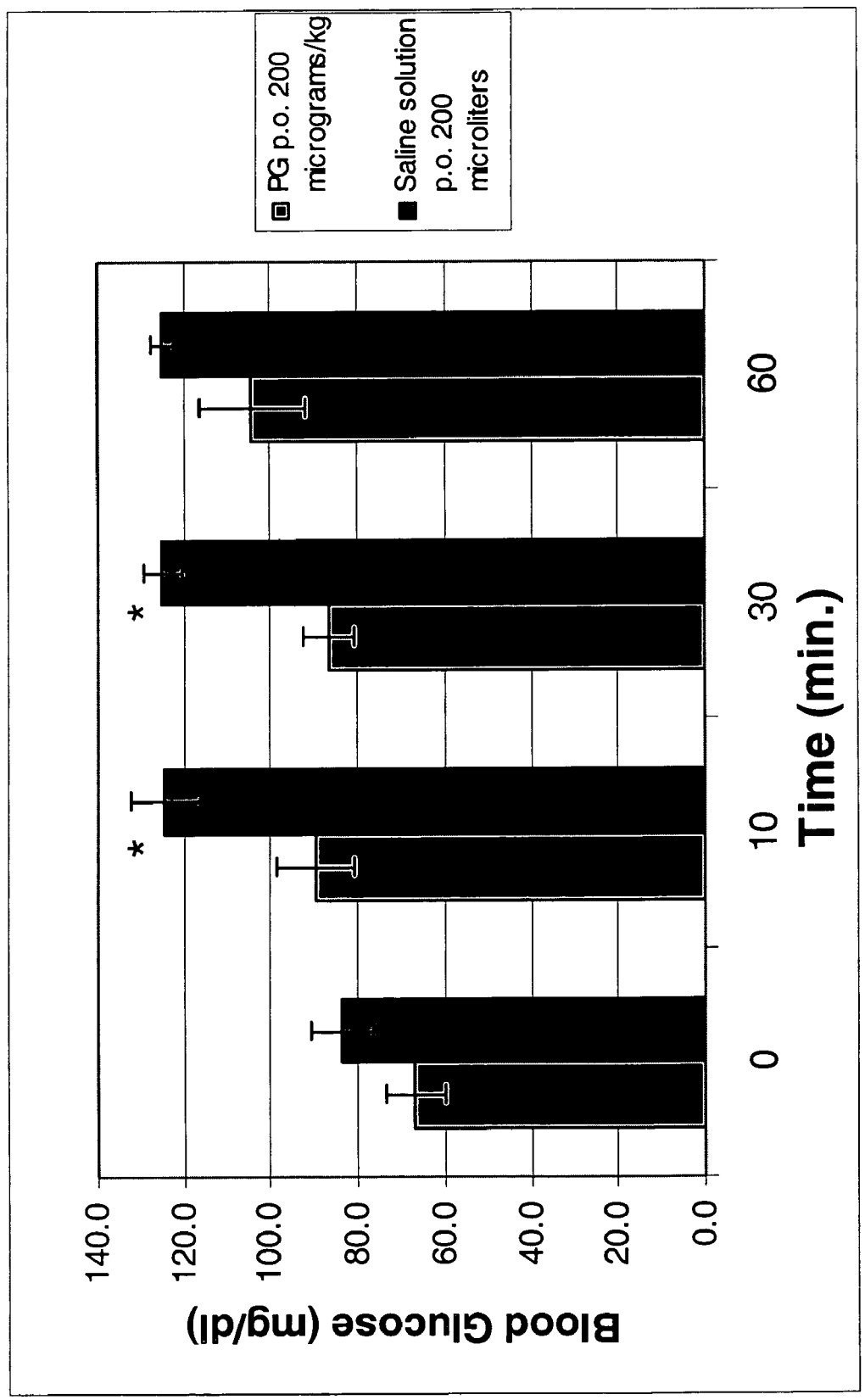
FIG. 6 shows the glucose blood levels in rats challenged with oral PG.

The observed effects of stimulation of gastric acid secretion may occur by different mechanisms. PG may be digested by gastric enzymes and the resulting free amino acids may stimulate acid secretion directly. Alternatively, the intact peptide may be actually absorbed from the gastric lumen and exert its effect on CCK-B receptors on the ECL and parietal cells. Of relevance, previous studies demonstrated that stimulation of CCK B receptors may lead to the secretion of pancreatic insulin (Abren et al., Diabetologia 81, 20(1):54-9). Additional studies demonstrated that CCK-B, which is the receptor for gastrin and pentagastrin, is the dominant form that is expressed in the pancreas (Funakoshi, A. et al., Digestion 1999 60 suppl. 1:75-80; Nishimori, I. et al., Pancrease 1999 19(2):109-13). Since blood glucose levels reflect the activity of peripheral insulin, glucose levels were measured in the pylorus-ligated rats following the administration of PG or saline. These measurements served as a surrogate marker for PG-induced insulin release via activation of CCK-B receptors on the ECL and parietal cells. As shown in FIG. 6, blood glucose levels decreased in animals that were treated with PG via oral route, as compared to controls. This observation supports the notion that the PG was absorbed intact and thereby could directly exert its effect on gastric tissue and stimulate secretion of gastric acid. This data is of particular importance since it demonstrates that PG can penetrate intact into the mucous layer under in vivo conditions. Taken together, these studies demonstrate that in contrast to the current model, surprisingly, PG is absorbed intact, directly through the gastric mucosa.

B. Co-Administration of PG and Omeprazole

Figure 7:
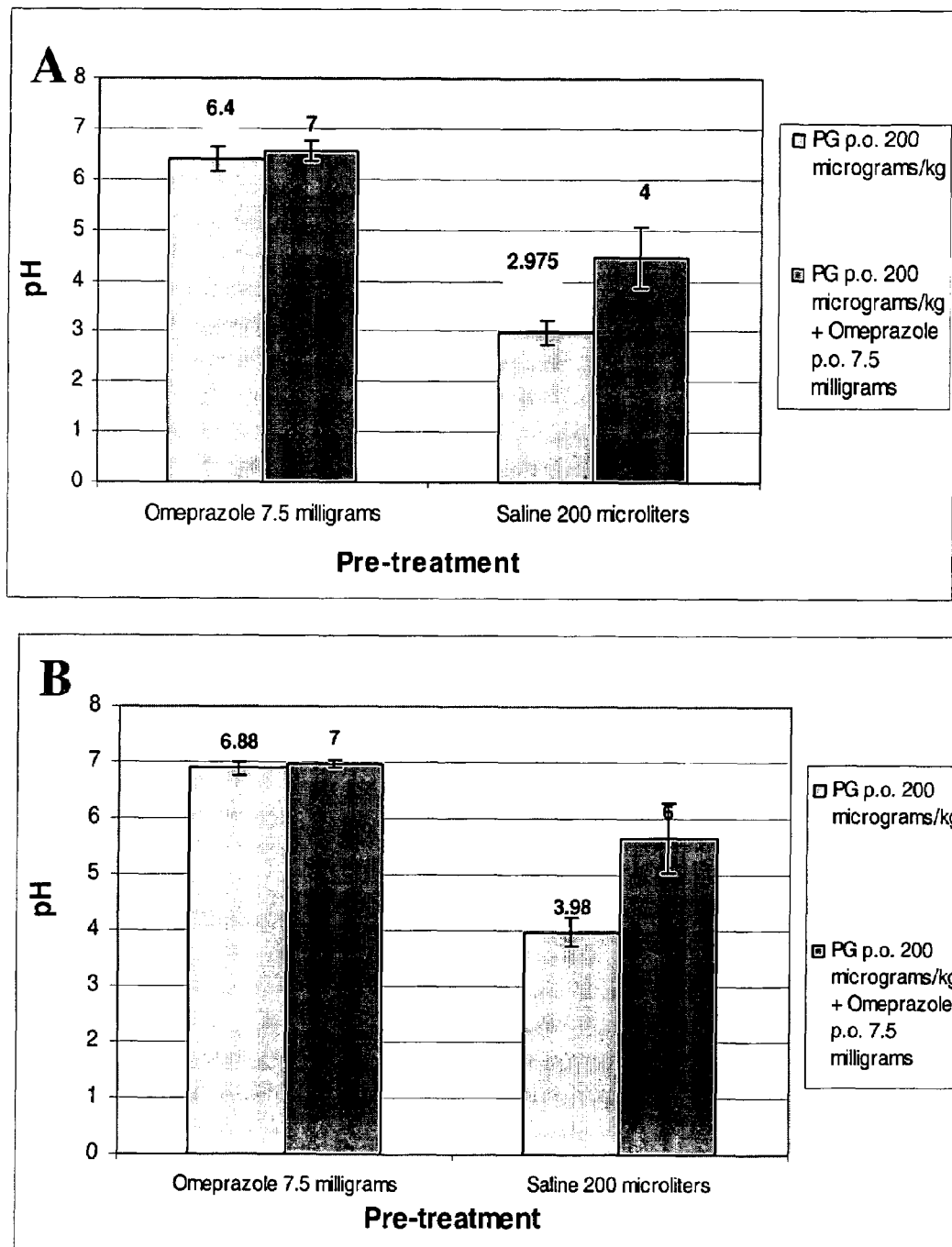
FIGS. 7A and 7B show the acid secretion following oral administration of PG in omeprazole or saline pre-treated rats. Gastric fluid was removed by puncture at 10 (A) and 30 (B) minutes, and the pH values were determined.
Figure 8:
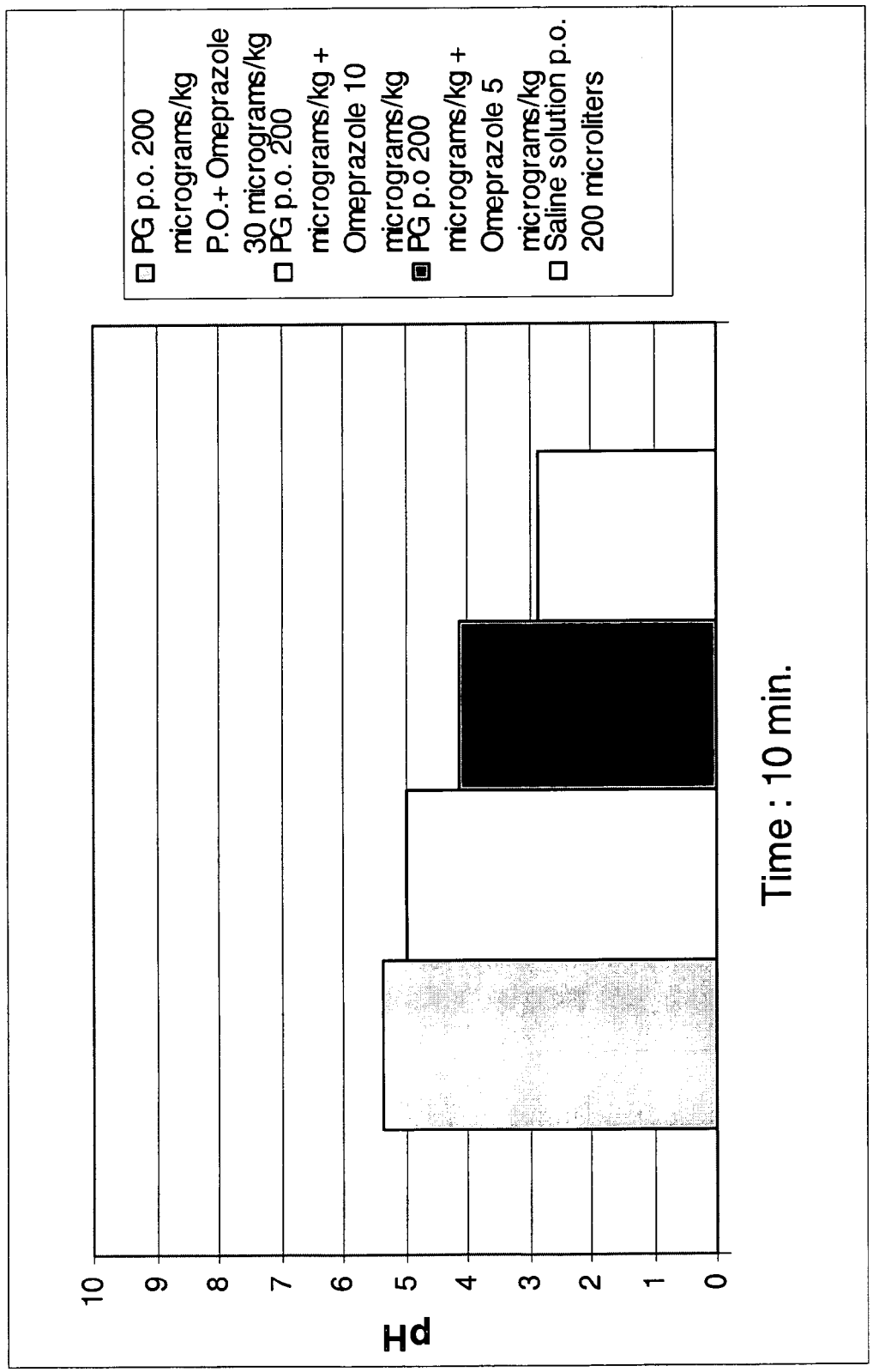
FIG. 8 shows the omeprazole dose-response study in conjunction with pentagastrin.

As shown, the combinations of omeprazole and PG or caerulein are potent means for the eradication of *H. pylori*. Furthermore, PPI agents are now accepted as a standard therapy for the eradication of *H. pylori*. Consequently, the inventors tested the effect on acid secretion of the co-administration of these agents. This information is vital for the assessment of the safety of such a combined treatment. Rats were pre-treated with omeprazole or saline suspended in propylene glycol, after which PG, or PG with omeprazole, were fed to the animals. Omeprazole 7.5 mg was pre-fed thirty minutes prior to PG administration, since in rodents the T½ of PPI is approximately 15 minutes (Regardh et al., Scand. J. Gastroenterol. Suppl. 1985 108:79-9). Taken together with the estimated time for absorption of omeprazole from the gastrointestinal tract, this experimental course was predicted to allow for an effective dosage of omeprazole while the PG exerted its acid-stimulating effect. As can be seen in FIGS. 7A and 7B, pre-treatment with oral omeprazole significantly inhibited gastric acid secretion ($p<0.05$). This effect was seen both at ten and thirty minutes post-stimulation. Suppression of acid secretion was profound when the omeprazole was given thirty minutes before PG. However, administration of PG at the same time as the omeprazole also suppressed acid secretion when compared to administration of PG alone. Thus, when animals were pre-fed with saline only, followed after thirty minutes by omeprazole and PG administration, acid secretion was lower than in the PG-only group (the results did not reach statistical significance [$p=0.07$], probably because of the small number of animals, but the trend is consistent with such an effect). The more potent inhibition of acid secretion in the animals that were pre-fed with omeprazole may result merely from the double dose of PPI. Such a possibility is supported by the results shown in FIG. 8, in which oral administration of different doses of omeprazole (30, 10, and 5 mg/kg) in combination with pentagastrin (200 µg/kg, without pre-treatment) showed a good dose-response correlation. These observations support the feasibility of treatment of *H. pylori* infection by administration of PG, since the standard co-therapy with a PPI agent allows for the suitable pH that is necessary for the healing of the ulcer crater.

Example 6 pH-Dependent Solubility of PG.

Figure 9A:
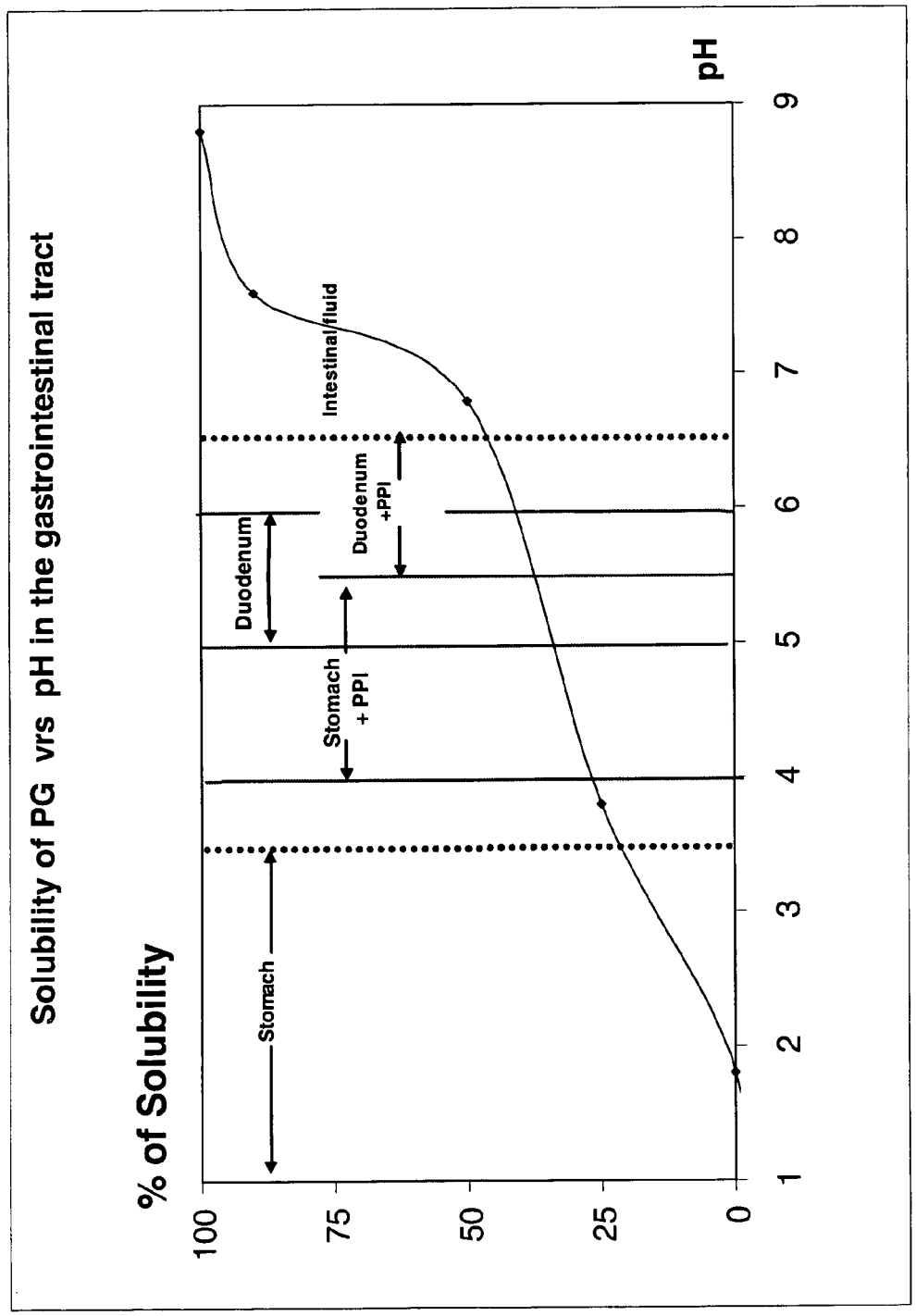
FIG. 9A shows the solubility of pentagastrin in various pH levels.

A major factor for the success of oral administration of PG is the optimization of delivery under the conditions that prevail in the gastric milieu. Shown in FIG. 9A are the results of the solubility of pentagastrin under various pH conditions. The results are represented in correlation to a gradient of relevant metabolic pH values within the gastric milieu, including values that are expected to occur following PPI treatment. The lowest level of solubility in pH 1.2 with NaCl was 40 ppm (all experiments were done with this concentration), and a marked increase was observed with escalating pH values. These results further support the feasibility of oral administration of PG in conjunction with omeprazole, or with other compounds which increase the pH of gastric fluids.

Example 7

Acid-Dependent and Pepsin-Dependent Degradation of PG.

Figure 9B:
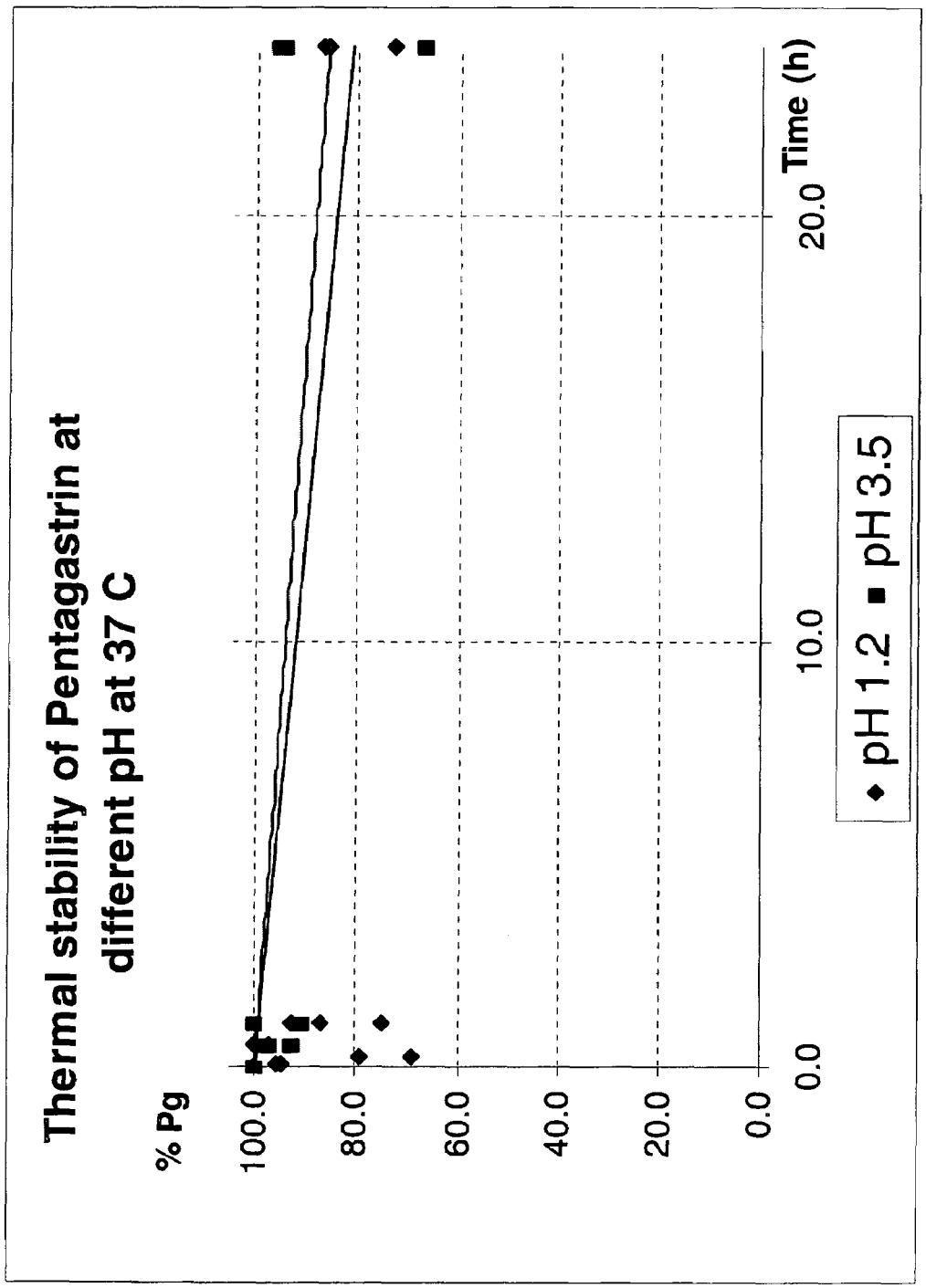
FIG. 9B shows the stability of Pentagastrin at different pHs at 37° C.

To test the effect of enzymatic degradation, the HCL-dependent degradation of PG without pepsin was tested at pH 1.2 and 3.5, at 37° C. As shown in FIG. 9B, in the absence of pepsin, there is a sharp degradation at the beginning of the reaction, with a maximum loss of 40% of pentagastrin. The main product of degradation (>80% of all products) corresponds to the standard of pentapeptide without BOC (RT=8.83). Such a fragment will still be active in the eradication of *H. pylori*.

Pepsin precipitation was tested using a spectrophotometer (USP). Under this condition of precipitation, an almost 100% pepsin precipitation was observed. Pentagastrin recovery was tested on HPLC by adding organic solvent to the pH 1.2 samples at time=0. An average of seven experiments resulted in 98.3% recovery of PG from the mixture after pepsin precipitation at time=0.

Figure 9C:
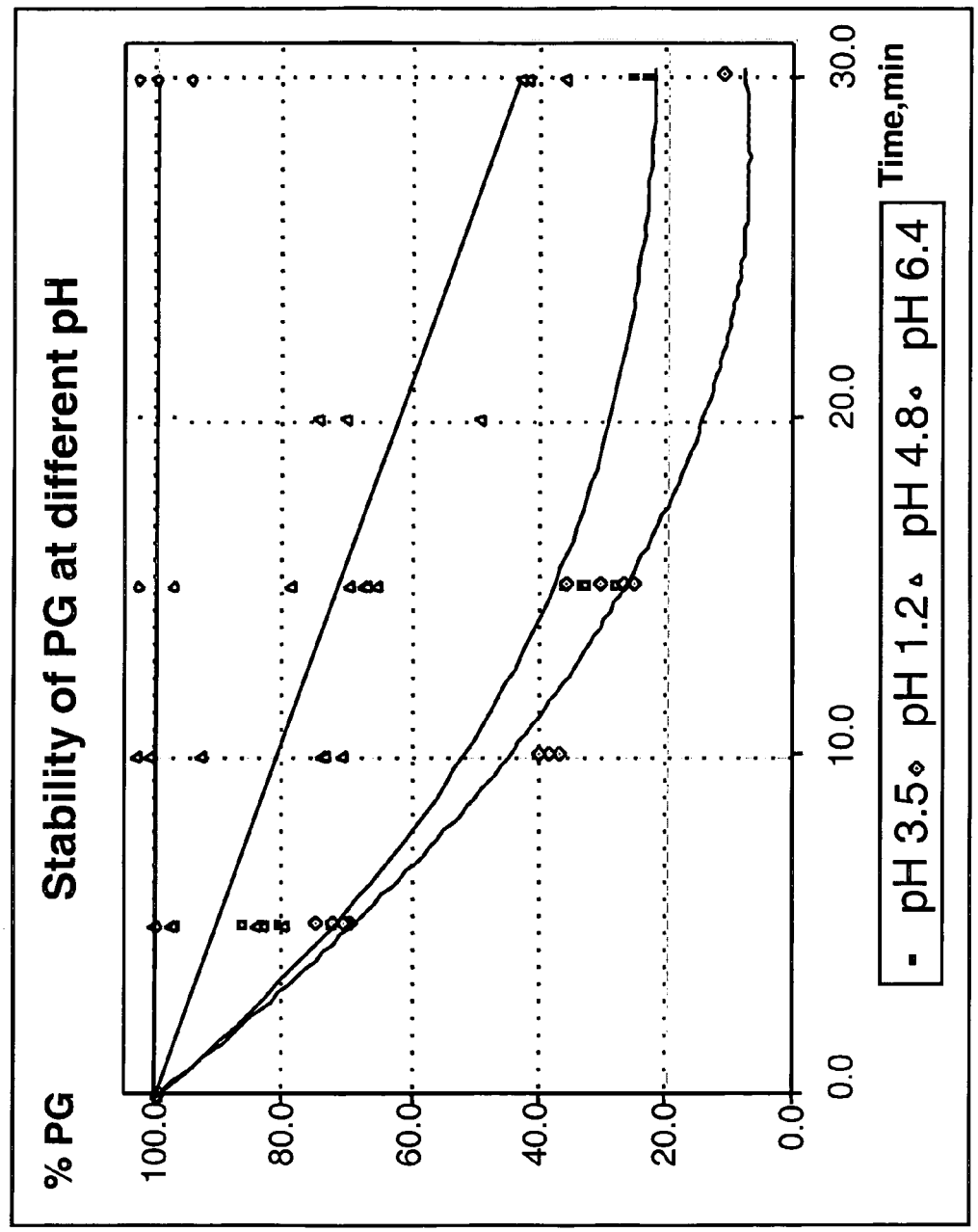
FIG. 9C shows the stability of Pentagastrin at various pHs in the presence of pepsin.

As shown in FIG. 9C, enzymatic degradation of the peptide is both pH- and time-dependent. At pH 1.2-3.5, optimal for pepsin activity, results are very similar. In this range, degradation rates 30%, 50%, and 70% were observed at 5, 10, and 15 minutes, respectively.

At pH 6.4, pentagastrin showed almost no degradation during 30 minutes. At pH 4.7, which is the most relevant for PPI-treated stomachs, very inconsistent results were observed, probably because of pepsin pK kinetics. Nevertheless, the average data is satisfactory, with more than 50% of non-degraded compound, even after 20 minutes of incubation.

Figure 10:
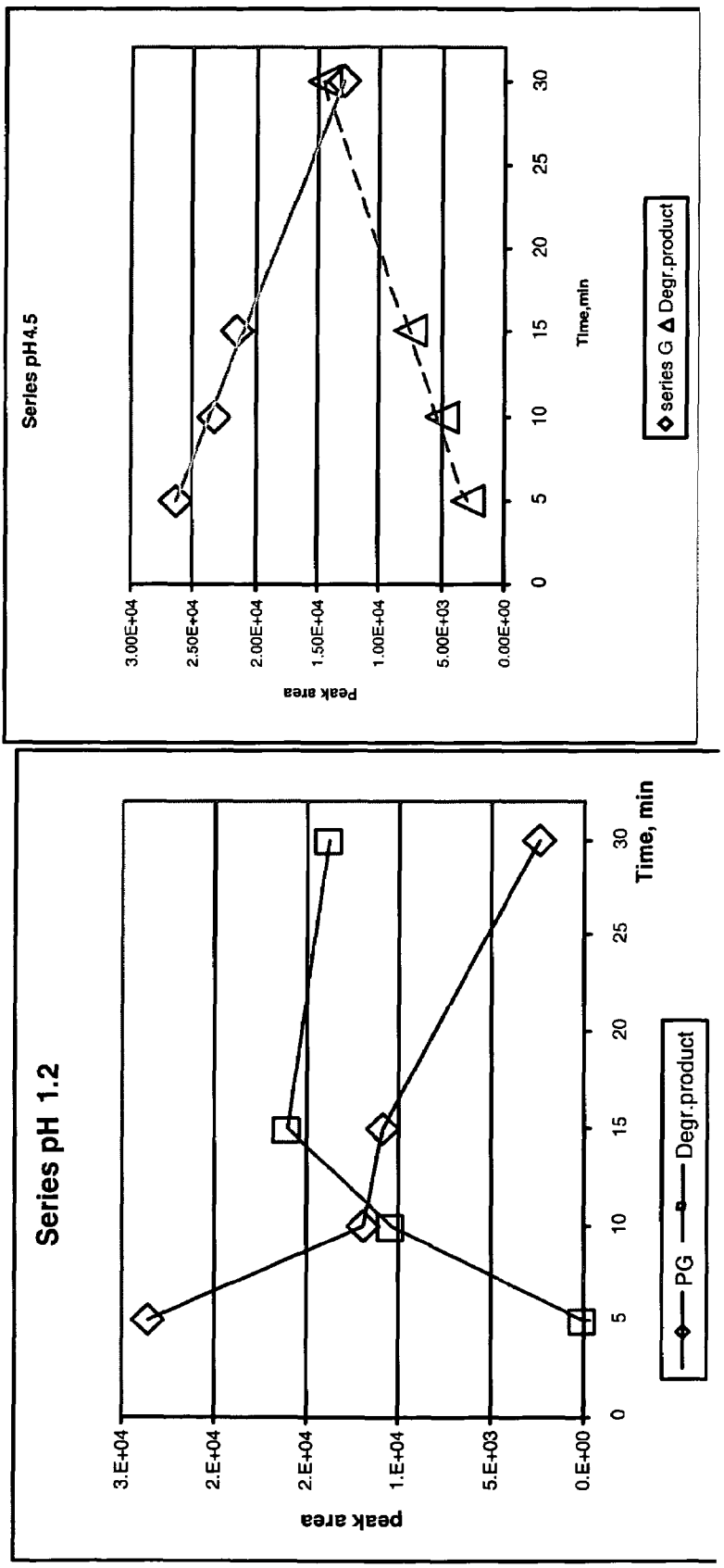
FIG. 10A and 10B show the correlation between decrease of levels of PG (-◇-) and increase of degradation product at pH 1.2 (A) and 4.5 (B).
Figure 11:
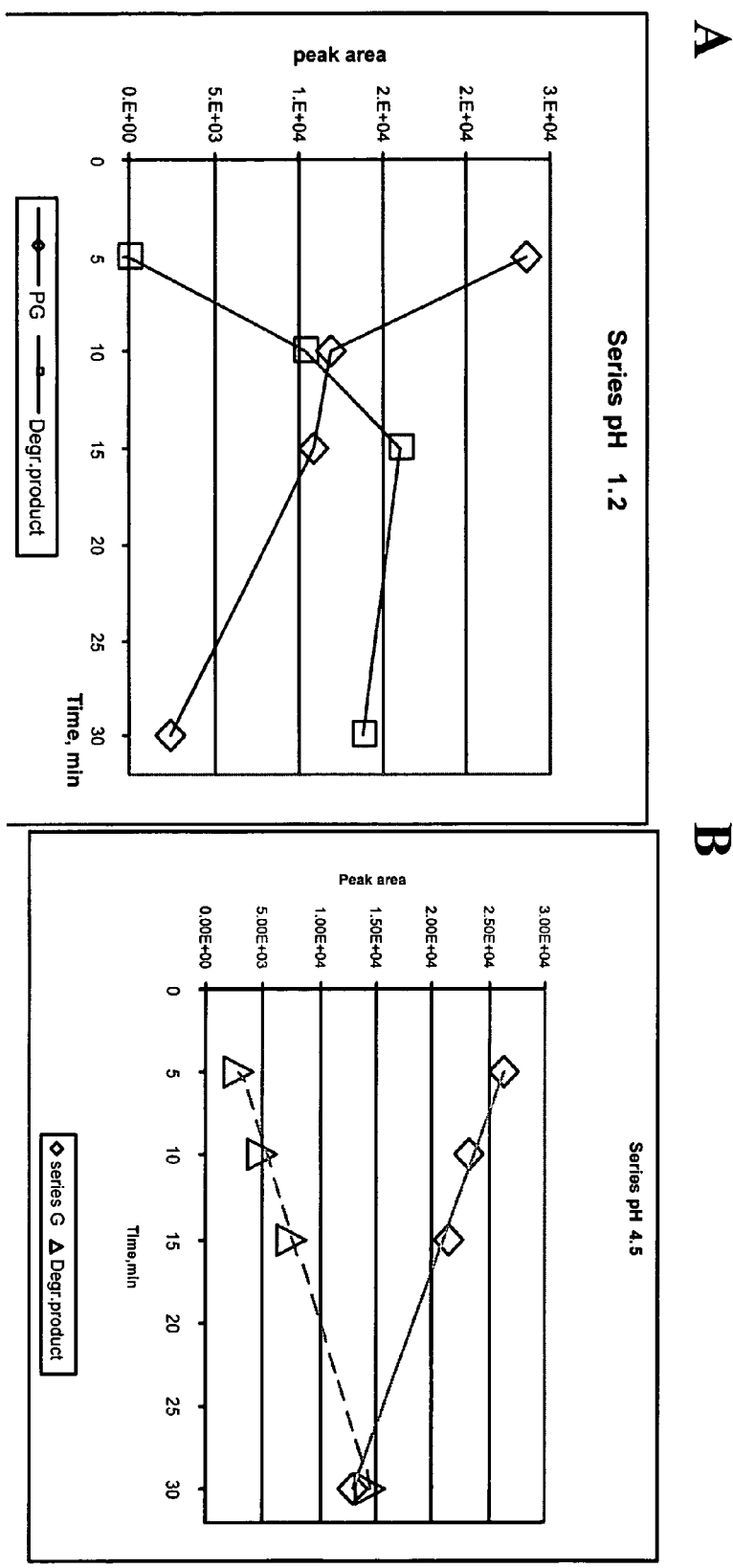

The concentration of the degradation product increases according the PG degradation, as shown in FIGS. 10A and 10B.

To summarize, PG is stable at different low pHs at 37° C.; therefore, the acidity alone should not alter its bioactivity at all. However, it is obvious that pepsin-mediated degradation leads to the generation of a non-active metabolite. The rate of production of this metabolite is pH-dependent and is correlated with pepsin activity in acidic pH. A promising fact is that at pH>4.5, the kinetics of degradation of PG leave a window for its biological activity. This pH is within the physiological pH range of gastric fluids under PPI treatment. In addition, the solubility of PG under pH mimicking the PPI-mediated effect has good potential.

It will be appreciated by a person skilled in the art that the present invention is not limited by what has been particularly shown and described hereinabove. Rather, the scope of the invention is defined by the claims that follow.

---

---

What is claimed is:

1. A method of reducing gastric acid secretion in a mammal in need thereof, the method comprising orally administering to the mammal a single unit oral dose comprising:
   a peptide comprising SEQ ID NO: 1 and
   an effective amount of proton pump inhibitor (PPI), wherein the peptide is in an immediate release form for release in the stomach and is in an amount sufficient to act locally in the stomach to reduce gastric acid secretion in conjunction with the PPI, whereas the PPI is in a delayed release form.

2. The method of claim 1, wherein the mammal has a pathology in which suppression of gastric acid secretion is required, wherein the pathology is selected from the group consisting of: reflux esophagitis, gastritis, duodenitis, gastric ulcer, duodenal ulcer, ulcer-related pathologies associated with administration of nonsteroidal anti-inflammatory drugs (NSAID), non-ulcer Dyspepsia, gastro-esophageal reflux disease, acute upper gastrointestinal bleeding, stress ulceration, *Helicobacter* infections, Zollinger-Ellison syndrome (ZES), Werner's syndrome, and systemic mastocytosis.

3. The method of claim 1, wherein the single unit dose further comprises a bio-adhesive agent in the immediate-release form in an amount sufficient to increase the local activity of the peptide in the stomach.

4. The method of claim 3, wherein the PPI is enteric coated and selected from the group consisting of: rabeprazole, omeprazole, isomeprazole, lansoprazole, pantoprazole, leminoprazole, single enantiomers thereof, alkaline salts thereof and mixtures thereof.

5. The method of claim 4, wherein the enteric coating comprises cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, or mixtures thereof.

6. The method of claim 1, wherein the mammal is a human and the peptide is pentagastrin (PG) administered orally in an amount of about 2.5 to 20 mg a day.

7. The method of claim 1, wherein the single unit dose further comprises an antibiotic or a protease inhibitor.

8. The method of claim 1, wherein the single unit dose is a tablet or capsule.

9. The method of claim 8, wherein the tablet is at least a double-layered tablet comprising a first layer comprising the peptide and a bio-adhesive agent and a second layer comprising PPI.

10. The method of claim 9, wherein the first layer is an outlayer of the tablet and the second layer is an inner layer surrounded by at least the first layer.

11. The method of claim 8, wherein the PPI is coated on a substrate and the PPI and substrate are enteric coated.

12. The method of claim 11, wherein the enteric coated PPI and substrate is coated with the peptide.

13. A method of reducing gastric acid secretion in a mammal in need thereof, the method comprising orally administering to the mammal a peptide comprising SEQ ID NO: 1 in conjunction with an effective amount of a proton pump inhibitor (PPI), wherein the peptide is administered in an immediate release oral form for release in the stomach, and the PPI is enteric coated and is selected from the group consisting of: rabeprazole, omeprazole, isomeprazole, lansoprazole, pantoprazole, leminoprazole, single enantiomers thereof, alkaline salts thereof and mixtures thereof, and wherein the peptide is in an amount sufficient to act locally in the stomach to reduce gastric acid secretion in conjunction with the PPI, thereby reducing gastric acid secretion in the mammal.

14. The method of claim 13, wherein the mammal is human and the peptide is pentagastrin (PG) administered orally in an amount of about 2.5 to 5 mg a day.

15. The method of claim 14, wherein the peptide is the N-protected derivative of PG selected from methoxymethyl (MOM), β-methoxyethoxymethyl (MEM), trialkylsilyl, triphenylmethyl (trityl), tert-butoxycarbonyl (t-BOC), ethoxyethyl (EE), fluorenyl-methoxycarbonyl (F-MOC), and trichloroethoxycarbonyl (TROC).

16. The method of claim 13, wherein the mammal has a pathology in which suppression of gastric acid secretion is required, wherein the pathology is selected from the group consisting of: reflux esophagitis, gastritis, duodenitis, gastric ulcer, duodenal ulcer, ulcer-related pathologies associated with administration of nonsteroidal anti-inflammatory drugs (NSAID), non-ulcer Dyspepsia, gastro-esophageal reflux disease, acute upper gastrointestinal bleeding, stress ulceration, *Helicobacter* infections, Zollinger-Ellison syndrome (ZES), Werner's syndrome, and systemic mastocytosis.

17. The method of claim 13, wherein the peptide is administered simultaneously, prior to, or following the administration of the PPI.

18. A method of reducing gastric acid secretion in a mammal in need thereof, the method comprising orally administering to the mammal a peptide comprising SEQ ID NO: 1 and a bio-adhesive agent in conjunction with an effective amount of a proton pump inhibitor (PPI), wherein the peptide, the bio-adhesive agent, and the PPI are in a single unit dosage form, wherein the peptide and bio-adhesive agent are in an immediate release form for release in the stomach and are in an amount sufficient to act locally in the stomach to reduce gastric acid secretion in conjuction with the PPI, and wherein the PPI is in a delayed release form for release in the intestine.

19. The method of claim 18, wherein the bio-adhesive agent is selected from the group consisting of: carbopol, methacrylic copolymer, chitosan, carboxymethylcellulose (CMC), or polyox.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial
<220> FEATURE:
<223> OTHER INFORMATION: Synthetic Peptide

<400> SEQUENCE: 1

Trp Met Asp Phe
1

<210> SEQ ID NO 2
<211> LENGTH: 5
<212> TYPE: PRT
<213> ORGANISM: Artificial
<220> FEATURE:
<223> OTHER INFORMATION: Synthetic Peptide

<400> SEQUENCE: 2

Ala Trp Met Asp Phe
1               5
```